(12) United States Patent
James et al.

(10) Patent No.: US 11,317,936 B2
(45) Date of Patent: May 3, 2022

(54) ULTRASONIC SURGICAL HANDPIECE ASSEMBLY

(71) Applicant: Stryker Corporation, Kalamazoo, MI (US)

(72) Inventors: Megan James, Portage, MI (US); Cathal Heavey, Midleton (IE); Guillaume Gras, Muenchenbuchsee (CH); Conor McCarthy, Cork (IE)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/580,639

(22) Filed: Sep. 24, 2019

(65) Prior Publication Data

US 2020/0093507 A1    Mar. 26, 2020

Related U.S. Application Data

(60) Provisional application No. 62/735,445, filed on Sep. 24, 2018.

(51) Int. Cl.
  *A61B 17/32* (2006.01)
  *A61B 90/98* (2016.01)
  *A61B 17/00* (2006.01)

(52) U.S. Cl.
  CPC ...... *A61B 17/320068* (2013.01); *A61B 90/98* (2016.02); *A61B 2017/00017* (2013.01);
  (Continued)

(58) Field of Classification Search
  CPC .. A61B 17/320068; A61B 2017/32007; A61B 2017/320069; A61B 2017/00017;
  (Continued)

(56) References Cited

U.S. PATENT DOCUMENTS 4,516,398 A    5/1985  Wuchinich
4,562,838 A    1/1986  Walker
(Continued)

FOREIGN PATENT DOCUMENTS

CA    2359426 C    6/2010
JP    2003093401 A    4/2003
(Continued)

OTHER PUBLICATIONS

International Search Report for Application No. PCT/US2019/052609 dated Mar. 20, 2020, 4 pages.
(Continued)

*Primary Examiner* — Ashley L Fishback
(74) *Attorney, Agent, or Firm* — Howard & Howard Attorneys PLLC

(57) ABSTRACT

The present disclosure relates to an ultrasonic surgical handpiece assembly comprising a surgical handpiece for use with an irrigation sleeve and ultrasonic tip. The surgical handpiece may comprise a piezoelectric transducer disposed within a housing and configured to manipulate the ultrasonic tip. One or more lumens and/or a flex circuit including an antenna may be disposed within the surgical handpiece housing. The lumen(s) may be configured to provide irrigation and/or aspiration to the irrigation sleeve and/or ultrasonic tip. The irrigation sleeve may comprise a second antenna configured to communicate with the ultrasonic handpiece antenna. The irrigation sleeve may further comprise and an alignment and/or coupling feature configured to removably secure the irrigation sleeve to the housing and orient the second antenna relative to the ultrasonic handpiece antenna. The irrigation sleeve may further comprise a lumen for supplying irrigation and/or aspiration to the ultrasonic tip.

20 Claims, 13 Drawing Sheets

(52) U.S. Cl.
CPC ............... *A61B 2017/00402* (2013.01); *A61B 2017/00477* (2013.01); *A61B 2017/32007* (2017.08); *A61B 2017/320069* (2017.08); *A61B 2017/320084* (2013.01)

(58) Field of Classification Search
CPC ........... A61B 2017/00402; A61B 2017/00477; A61B 2017/320084; A61B 90/98
See application file for complete search history.

(56) References Cited

U.S. PATENT DOCUMENTS

| | | | |
|---|---|---|---|
| 5,163,433 | A | 11/1992 | Kagawa et al. |
| 6,214,017 | B1 | 4/2001 | Stoddard et al. |
| 6,497,715 | B2 | 12/2002 | Satou |
| 6,896,672 | B1 | 5/2005 | Eggers et al. |
| 6,955,680 | B2 | 10/2005 | Satou et al. |
| 6,984,220 | B2 | 1/2006 | Wuchinich |
| 7,442,168 | B2 | 10/2008 | Novak et al. |
| 7,641,503 | B1 | 1/2010 | van der Horn et al. |
| 7,749,240 | B2 | 7/2010 | Takahashi et al. |
| 7,871,392 | B2 | 1/2011 | Sartor |
| 8,016,843 | B2 | 9/2011 | Escaf |
| 8,546,999 | B2 | 10/2013 | Houser et al. |
| D796,667 | S | 9/2017 | Manandhar et al. |
| 2003/0199794 | A1 | 10/2003 | Sakurai et al. |
| 2015/0005796 | A1 | 1/2015 | Isola et al. |
| 2016/0242961 | A1 | 8/2016 | DeTurk et al. |
| 2017/0071621 | A1 | 3/2017 | Downey et al. |
| 2017/0333606 | A1 | 11/2017 | Manandhar et al. |
| 2017/0340339 | A1 | 11/2017 | Madan et al. |
| 2017/0354429 | A1 | 12/2017 | Ketelhohn et al. |
| 2018/0056328 | A1 | 3/2018 | Downey et al. |
| 2018/0132885 | A1 | 5/2018 | Cotter et al. |
| 2019/0336161 | A1 | 11/2019 | Scheller et al. |
| 2020/0038046 | A1 | 2/2020 | Schwamb et al. |

FOREIGN PATENT DOCUMENTS

| | | |
|---|---|---|
| JP | 2003305050 A | 10/2003 |
| JP | 2005066316 A | 3/2005 |
| JP | 2010500073 A | 1/2010 |
| WO | 9524865 A1 | 9/1995 |
| WO | 2016022808 A1 | 2/2016 |

OTHER PUBLICATIONS

Partial International Search Report for Application No. PCT/US2019/052609 dated Jan. 8, 2020, 2 pages.

Reality RX Communication, "CUSA Clarity System Setup Video", Mar. 3, 2017, https://www.youtube.com/watch?v=M5aCRYmCQYA, 1 page.

English language abstract for JP 2003-093401 A extracted from espacenet.com database on Dec. 13, 2021, 1 page.

English language abstract for JP 2003-305050 A extracted from espacenet.com database on Dec. 13, 2021, 2 pages.

English language abstract for JP 2005-066316 A extracted from espacenet.com database on Dec. 13, 2021, 2 pages.

English language abstract for JP 2010-500073 A extracted from espacenet.com database on Dec. 13, 2021, 2 pages.

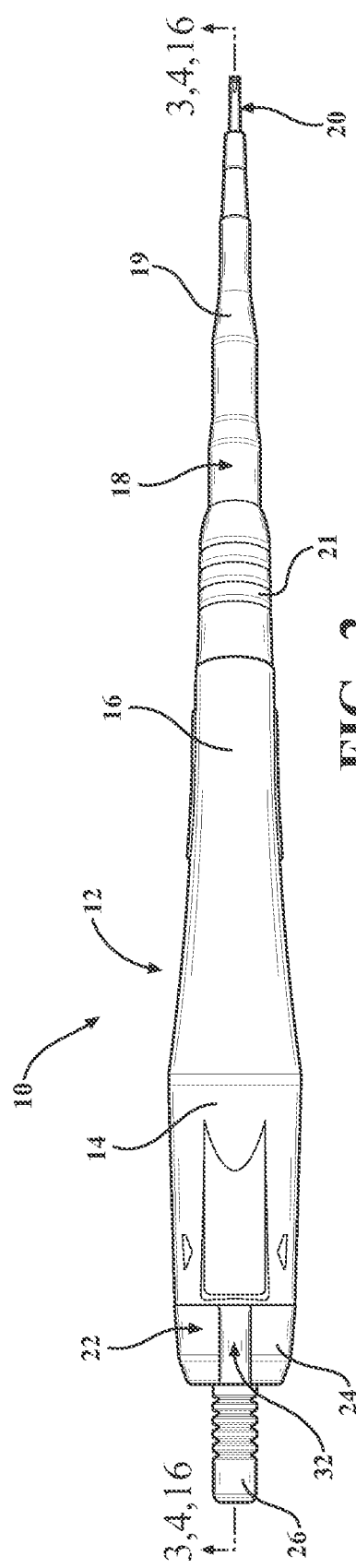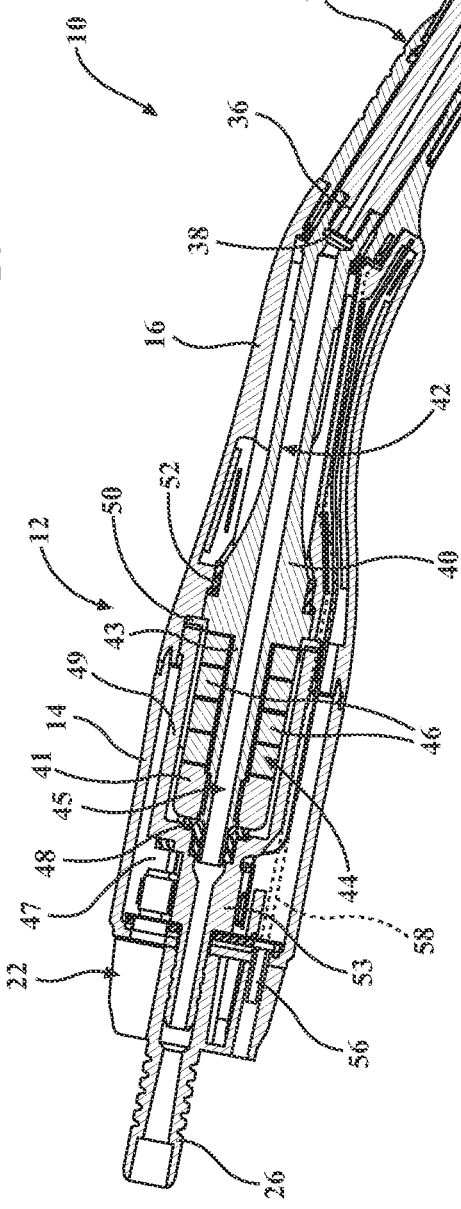

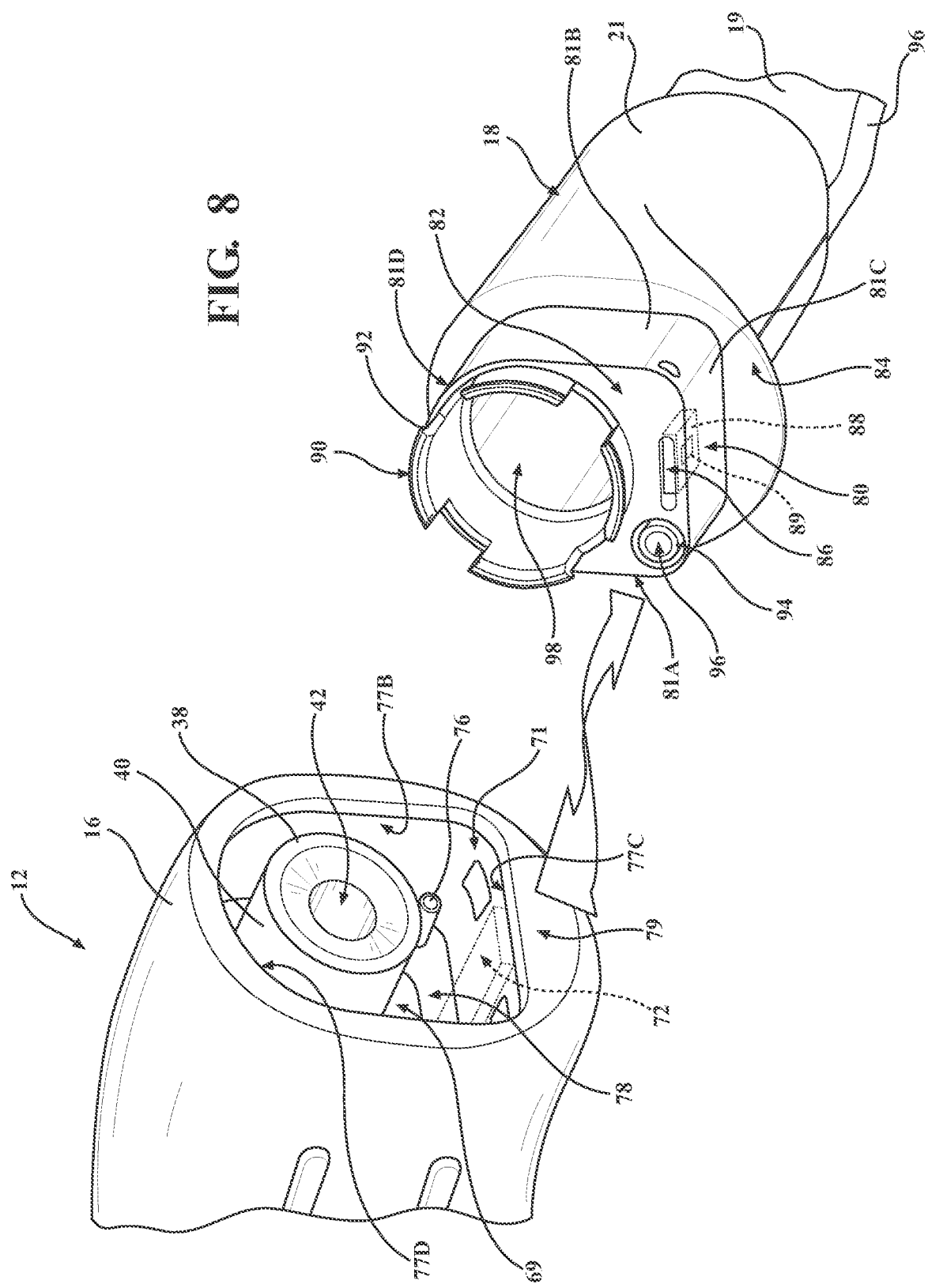

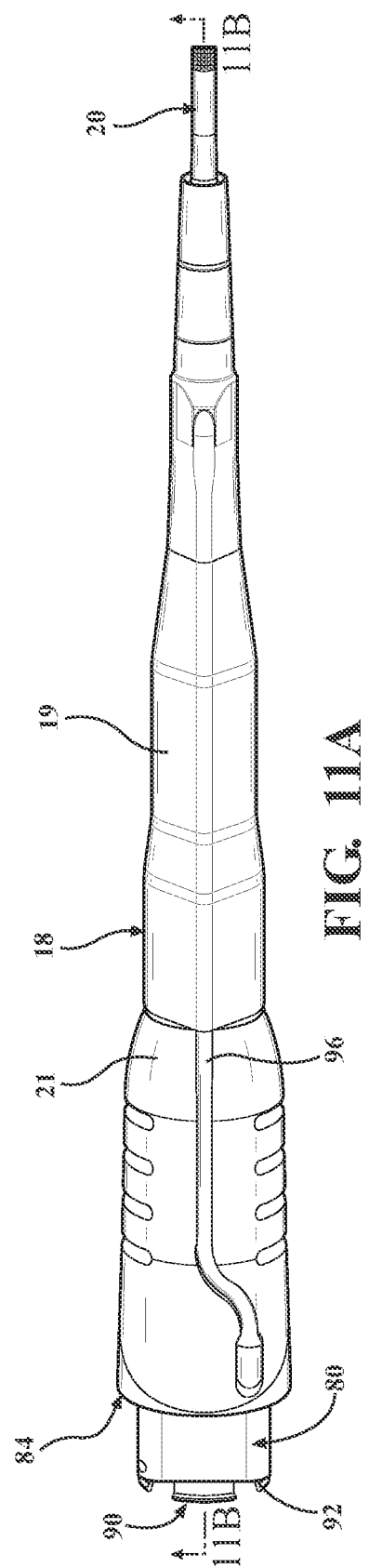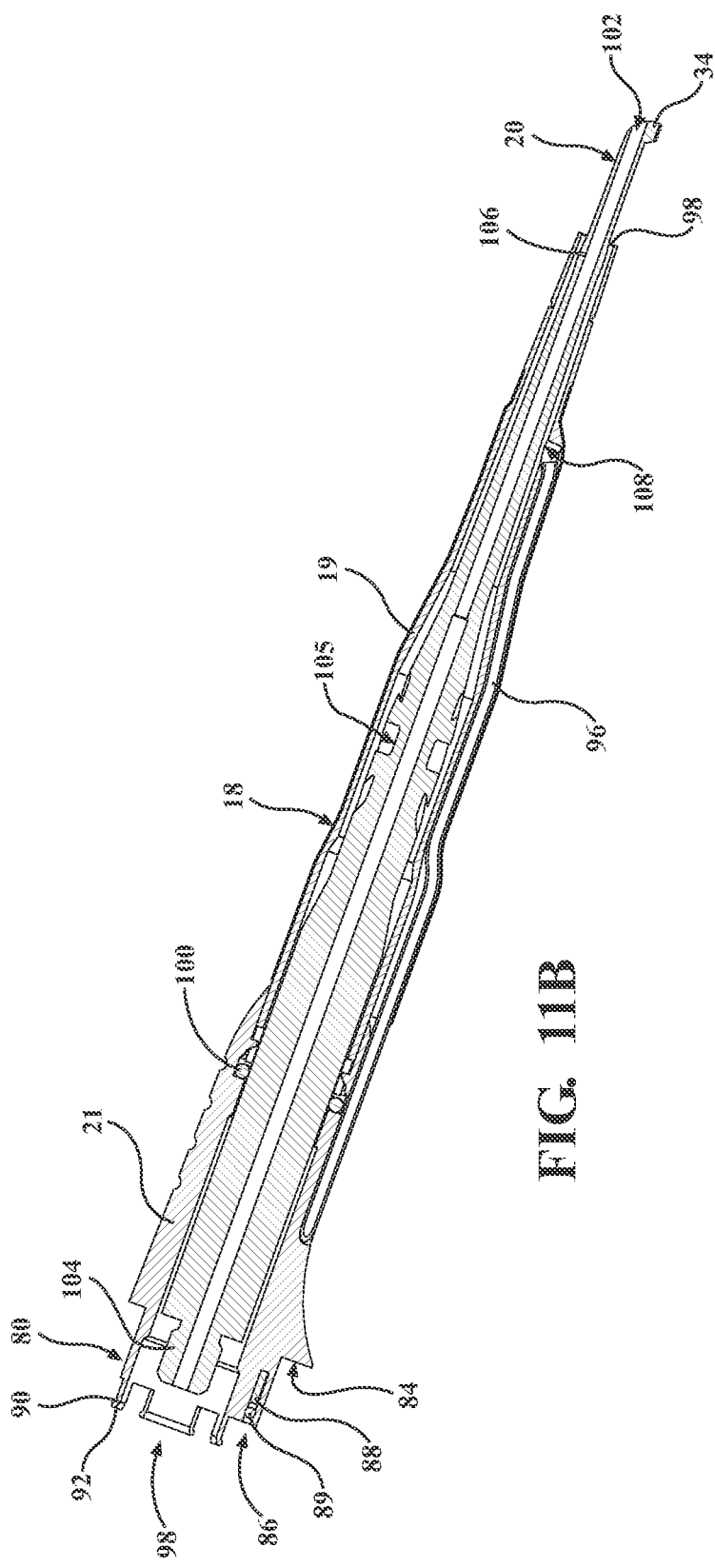

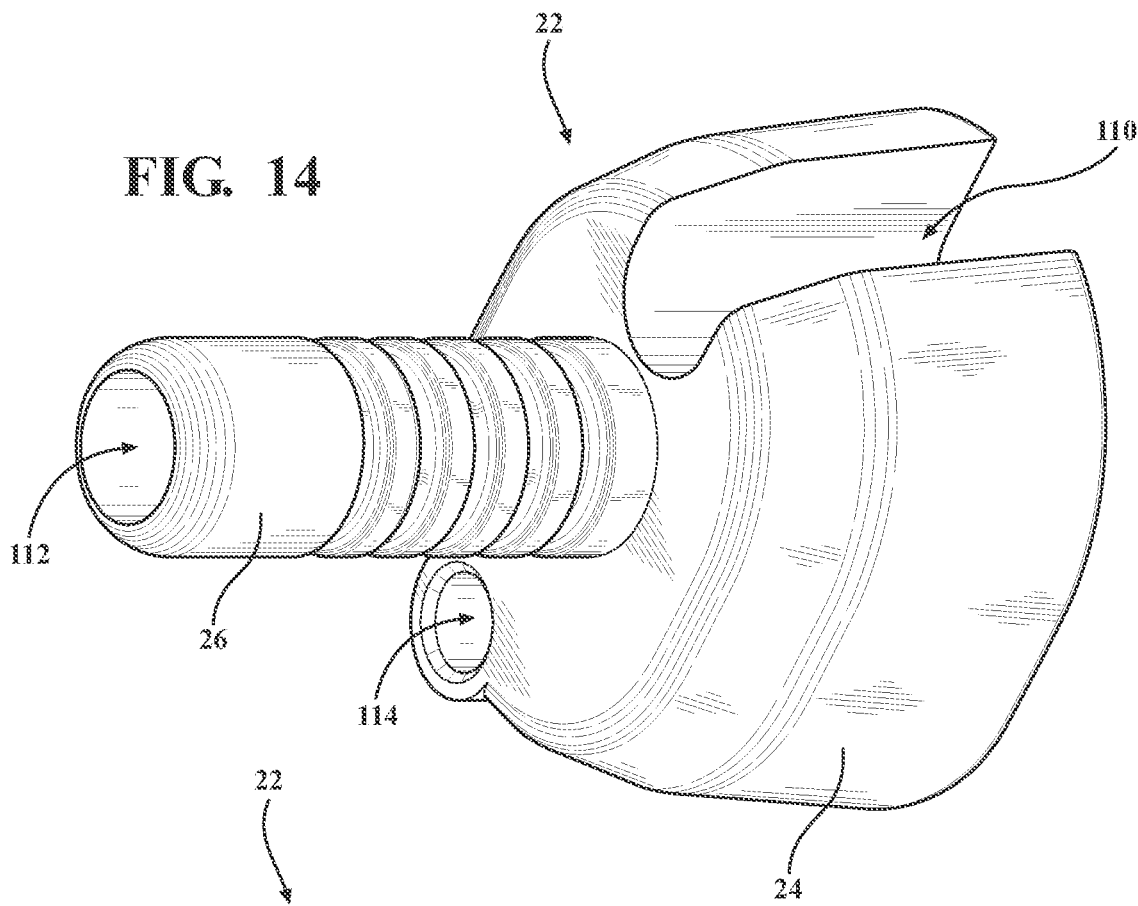
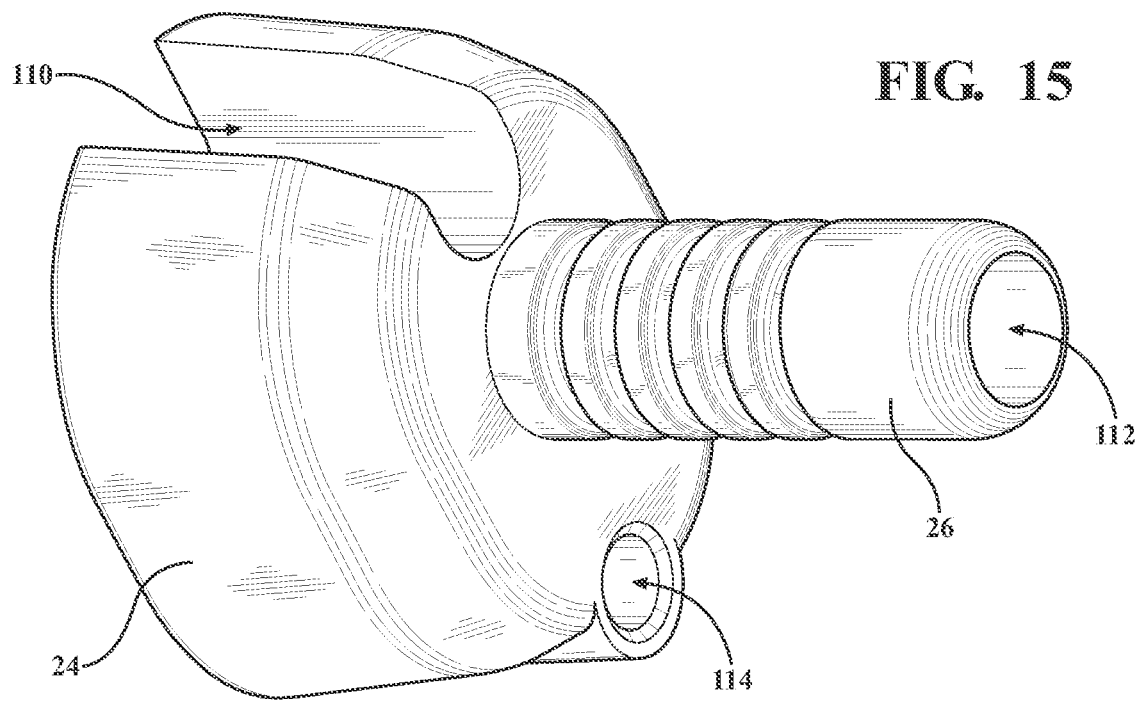

ULTRASONIC SURGICAL HANDPIECE ASSEMBLY

RELATED APPLICATIONS

This application claims priority to U.S. Application 62/735,445, filed on Sep. 24, 2018, which is hereby incorporated herein by reference in its entirety.

SUMMARY

The present disclosure relates generally to an ultrasonic surgical handpiece assembly. The ultrasonic surgical handpiece assembly may include a handpiece comprising a transducer and a horn, wherein the transducer is configured to manipulate the horn to actuate a cutting tip that is coupled to the horn to cut or remove biological material.

An exemplary configuration provides a sleeve for use with an ultrasonic handpiece including a coupling housing comprising a handpiece transceiver and configured to surround a portion of an ultrasonic tip including a cutting feature. The sleeve may comprise a hub comprising a proximal portion, a distal portion, and a first lumen extending through the hub. The proximal portion may have a first face configured to abut the ultrasonic handpiece and a second face positioned distally of the first face. The sleeve may further comprise a tube body comprising a distal end and a proximal end. The tube body may extend from the distal portion of the hub and be configured to define a second lumen in fluid communication with the first lumen of the hub. The second lumen may be configured to surround the portion of the ultrasonic tip. The sleeve may also comprise a tube aperture in an interior surface of the second lumen. The tube aperture may be positioned at an intermediate point along the second lumen between the proximal end and distal end of the tube body and such that the tube aperture is facing inward towards the second lumen. An irrigation conduit may be adjacent to the second lumen, the irrigation conduit configured to extend from the proximal end of the tube body to the tube aperture. An irrigation aperture and a tip aperture in the first face, the tip aperture configured to be in communication with the first lumen. An irrigation fitting may be positioned within the irrigation aperture of the first face of the hub and in fluid communication with the irrigation tube. The sleeve may also comprise at least one retention finger protruding proximally from the first face, the retention finger configured to engage the coupling housing of the ultrasonic handpiece. The sleeve may further comprise a cavity defined in the proximal portion of the hub, the cavity comprising an opening in a first surface. A sleeve transceiver may be positioned within the cavity and configured to communicate with the corresponding handpiece transceiver.

In another exemplary configuration, an ultrasonic surgical handpiece may be configured for use with an ultrasonic tip assembly including a sleeve comprising at least one retention member. The ultrasonic surgical handpiece may comprise a housing comprising a proximal end and an opposing distal end, said housing configured to define a volume. The ultrasonic surgical handpiece may also comprise a transducer at least partially disposed within the volume defined by the housing, and a horn comprising a first end and an opposing second end. The horn may be configured to be at least partially disposed within the volume defined by the housing, the first end of said horn operatively coupled to the transducer. Wherein the transducer is configured to vibrate/oscillate the horn when operated. The ultrasonic surgical handpiece may also comprise an attachment region formed in the distal end of the housing. The attachment region may define a recess comprising a face and a plurality of side walls configured to receive the sleeve. An attachment element in the face of the recess, wherein the attachment element may be configured to receive the at least one retention member of the sleeve to removably couple the sleeve to the ultrasonic surgical handpiece. The ultrasonic surgical handpiece may further comprise a first fitting extending from the face of the recess and may be configured to removably couple with the sleeve to provide irrigation to the sleeve, and wherein the second end of the horn is configured to protrude from the face.

In yet another exemplary configuration, an ultrasonic handpiece assembly may be configured for use with an elongated cutting instrument including an aspiration lumen extending the length of the elongated cutting instrument. The assembly may comprise an ultrasonic handpiece comprising: a housing comprising a proximal end and an opposing distal end, the housing defining a volume and the distal end having a distal face. The handpiece may also comprise a transducer configured to define a first conduit, the transducer at least partially disposed within the volume defined by the housing. The handpiece may also comprise a horn comprising a first end and an opposing second end, the horn configured to be at least partially disposed within the volume defined by the housing. The horn may comprise a second conduit in said horn configured to extend between the first end and the second end of the horn. The horn may also comprise a threaded coupler on the second end of the horn configured to extend from the distal end of the housing and removably couple the horn to the elongated cutting instrument. The assembly may also comprise an irrigation outlet fitting extending from the distal end of the housing and configured to discharge irrigation fluid from the housing. The assembly may also comprise an irrigation sleeve The irrigation sleeve may comprise a hub defining a first lumen and comprising an irrigation inlet fitting, the irrigation inlet fitting configured to engage the irrigation outlet fitting to receive irrigation fluid discharged from the ultrasonic handpiece. The sleeve may also comprise a sleeve body extending distally from the hub, the sleeve body defining a second lumen configured to surround a portion of the elongated cutting instrument when the elongated cutting instrument is inserted into the irrigation sleeve. The sleeve may further comprise a tube aperture in an interior surface of the second lumen, the tube aperture positioned at an intermediate point along the second lumen between a proximal end and a distal end of the sleeve body such that the tube aperture is facing toward the second lumen to provide irrigation fluid to a surgical site and to cool the elongated cutting instrument. The sleeve may also comprise an irrigation conduit running adjacent to the second lumen, the irrigation conduit configured to extend from the irrigation inlet fitting of the sleeve body to the tube aperture to create a fluid passageway for communicating irrigation fluid to the elongated cutting instrument, wherein the irrigation outlet fitting on the housing may be configured to engage the irrigation inlet fitting on the irrigation sleeve when the irrigation sleeve is coupled to the housing such that the irrigation fluid flows entirely within the ultrasonic handpiece and the hub. Furthermore, the first end of the horn may be operatively coupled to the transducer such that the first conduit of the transducer and the second conduit of the horn may define a continuous passageway extending from the proximal end to the distal end of the housing.

In yet another exemplary configuration, an ultrasonic handpiece assembly may be configured for use with an elongated cutting instrument. The assembly may comprise an ultrasonic handpiece comprising a housing, a transducer, and a horn. The housing may comprising a proximal end and an opposing distal end, the housing defining a volume and the distal end having a distal face. The transducer may be configured to define a first conduit, the transducer at least partially disposed within the volume defined by the housing. The horn may comprise a first end and an opposing second end, the horn configured to be at least partially disposed within the volume defined by the housing. The horn may comprise a second conduit in the horn configured to extend between the first end and the second end of the horn. An irrigation outlet fitting extending from the distal end of the housing and configured to discharge irrigation fluid from the housing. A threaded coupler may be disposed on the second end of the horn configured to engage the elongated cutting instrument. There may be a recess in the distal end of the housing, the recess comprising a recessed face and a plurality of side walls configured to define an asymmetrical shape. The assembly may further comprise a handpiece transceiver comprising a handpiece coil comprising a first axis, the handpiece transceiver positioned within one of the plurality of side walls. The assembly may also comprise an irrigation sleeve comprising a hub comprising a proximal portion and a distal portion, the proximal portion configured to define an asymmetrical protrusion extending proximally from the distal portion and sized to be inserted within the recess of the housing. The irrigation sleeve may also comprise an abutment portion configured to contact the distal face of the ultrasonic handpiece when the asymmetrical protrusion is inserted in the recess of the housing. The asymmetrical protrusion may be configured to ensure proper alignment of the irrigation sleeve with the housing. The irrigation sleeve may further comprise a sleeve transceiver comprising a sleeve coil and a memory unit, the memory unit storing information pertaining to the optimal driving parameter for the elongated cutting instrument. The sleeve coil may have a second axis, wherein the sleeve transceiver is located in a cavity defined in the asymmetrical protrusion of the hub such that the second axis of the sleeve coil is oriented in parallel to the first axis of the handpiece coil.

In yet another exemplary configuration, a tubing connector may be configured for integrally connecting an irrigation line, an aspiration line, and a conductor to a proximal portion of an ultrasonic surgical handpiece wherein the ultrasonic surgical handpiece comprises an irrigation fitting and an aspiration fitting that extend proximally from the proximal portion of the handpiece. The tubing connector may comprise a base comprising a distal end and a proximal end. The tubing connector may also comprise a first lumen in said base configured to create a fluid passageway through the base that extends from the distal end to the proximal end of the base. The first lumen may be configured to receive the aspiration line proximate the proximal end of the base. The base may define a groove in a perimeter of the base that extends between the proximal region to the distal region of the base, the groove configured to receive the conductor. A portion of the first lumen proximate the distal end of the base is configured to removably couple with the aspiration fitting of the ultrasonic surgical handpiece via a friction fit, and wherein the tubing connector is configured to reduce strain of the irrigation line and the aspiration line when coupled to the surgical handpiece.

These and other configurations, features, and advantages of the present disclosure will be apparent to those skilled in the art. The present disclosure is not intended to be limited to or by these configurations, embodiments, features, and/or advantages.

BRIEF DESCRIPTION OF THE DRAWINGS

Referring now to the drawings, exemplary illustrations are shown in detail. Although the drawings represent schematic embodiments, the drawings are not necessarily to scale and certain features may be exaggerated to better illustrate and explain an innovative aspect of an illustrative embodiment. Further, the exemplary illustrations described herein are not intended to be exhaustive or otherwise limiting or restricting to the precise form and configuration shown in the drawings and disclosed in the following detailed description.

Advantages of the present invention will be readily appreciated as the same becomes better understood by reference to the following detailed description when considered in connection with the accompanying drawings wherein:

FIG. 2 is a top view of the ultrasonic surgical handpiece assembly of FIG. 1.

FIG. 3 is a sectional view of the ultrasonic surgical handpiece assembly of FIG. 1.

FIG. 8 is a partially exploded view of the ultrasonic surgical handpiece assembly of FIG. 1, illustrating an example configuration of an interface between the front housing portion of the ultrasonic handpiece and the irrigation sleeve.

FIG. 11A is a bottom view of the irrigation sleeve and the ultrasonic tip of FIG. 10.

FIG. 11B is a sectional view of the irrigation sleeve and the ultrasonic tip of FIG. 10.

FIG. 14 is a second perspective view of the tubing connector of FIG. 12.

FIG. 15 is a third perspective view of the tubing connector of FIG. 12.

DETAILED DESCRIPTION

As medical professionals strive for reducing the size of the incisions and the amount of recovery time required following invasive medical procedures, the size of medical instruments used in various medical procedures have become smaller. Many of the medical instruments utilized in performing the various medical procedures may include the use of a cutting accessory, such as ultrasonic handpieces, high-speed drills, rotating burs, open-window shavers, and the like. Many of these cutting accessories may require the use of irrigation or aspiration (i.e., suction) to reduce heat and/or remove debris at the surgical site. Similarly, irrigation may be utilized to lubricate a cutting accessory.

One example of a surgical instrument that may utilize irrigation and aspiration systems is an ultrasonic handpiece. Generally, one or more lines may be coupled to the ultrasonic handpiece to supply irrigation and suction. The ultrasonic handpiece may further comprise a sleeve comprising one or more lumens that may be utilized to direct fluid from an irrigation source toward the surgical site and the cutting accessory, i.e., an ultrasonic tip. Irrigation and/or aspiration lines have typically been coupled to the exterior of the ultrasonic handpiece to be coupled to the sleeve. The sleeve and/or cutting accessory may be disposable, resulting in the sleeve and/or cutting accessory only temporarily being attached to the ultrasonic handpiece. The introduction of additional elements, such as the irrigation and/or aspiration lines to the exterior of the handpiece can result in increasing the size, profile, and/or general bulkiness of the ultrasonic handpiece. This may obstruct the medical professional's view and/or distract the medical professional during operation of the medical instrument during the medical procedure. The positioning of the irrigation and/or aspiration lines relative to the ultrasonic handpiece may similarly effect the ergonomics of the ultrasonic handpiece, inhibiting the medical professional's ability to manipulate the ultrasonic handpiece.

Figure 1:
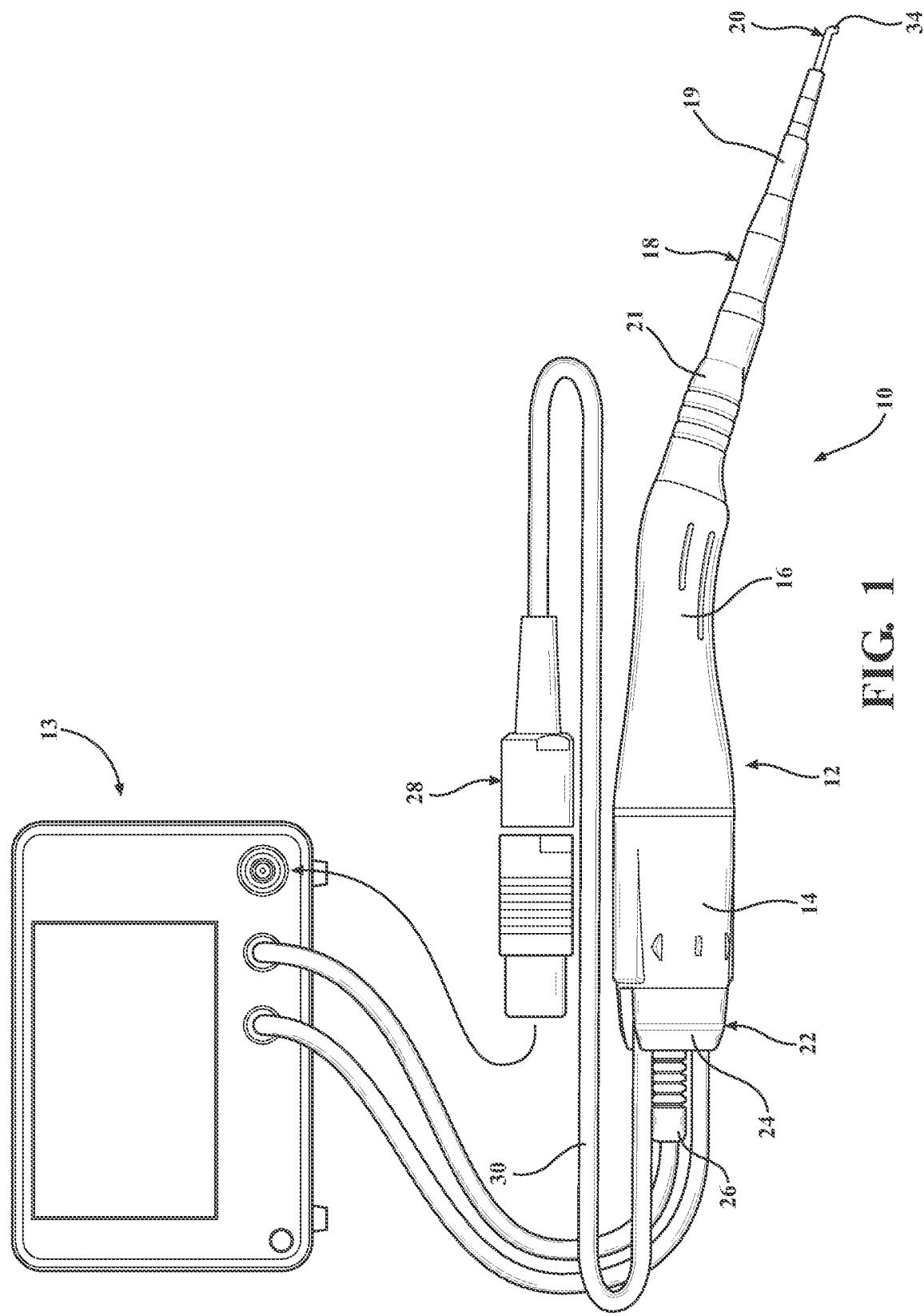
FIG. 1 is a side view of an ultrasonic surgical handpiece assembly, including an ultrasonic handpiece, an irrigation sleeve, an ultrasonic tip, and a control console.

Therefore, an ultrasonic surgical handpiece assembly 10 may be configured to comprise an ultrasonic handpiece 12 including internal irrigation and aspiration lumens to reduce the size of the handpiece and improve ergonomics, such as the ultrasonic surgical handpiece assembly 10 illustrated in FIGS. 1-3.

Referring to FIGS. 1 and 2, an example configuration of an ultrasonic surgical handpiece assembly 10 is illustrated. The ultrasonic surgical handpiece assembly 10 may comprise an ultrasonic handpiece 12 comprising a proximal end and distal end. The ultrasonic surgical handpiece assembly 10 may further comprise sleeve 18 and an ultrasonic tip 20 that may be coupled to the distal end of the ultrasonic handpiece 12. The sleeve 18 may be configured to provide irrigation to the ultrasonic tip 20 and/or the surgical site. It is further contemplated that the sleeve 18 may also be configured to provide aspiration to the ultrasonic tip 20. The ultrasonic tip 20 may comprise a cutting feature 34 that is configured to cut, shape, and/or remove biological tissue.

The ultrasonic tip 20 may have various features, as described in U.S. Pat. Nos. 6,497,715; 6,955,680; and 6,984,220; which are hereby incorporated herein by reference in their entirety.

The ultrasonic surgical handpiece assembly 10 may also comprise a cable 30 or other power cord comprising a power connector 28 or adapter configured to couple the ultrasonic surgical handpiece assembly 10 to a power supply, such as a control console 13 configured to regulate the various aspects of the ultrasonic handpiece 12. For example, the console 13 may be configured to regulate the power and the signal supplied to the ultrasonic handpiece 12. The console 13 may also be configured to regulate the irrigation and/or aspiration functions of the ultrasonic handpiece 12 to optimize performance of the ultrasonic surgical handpiece assembly 10.

Referring to FIG. 3, a sectional view of the ultrasonic surgical handpiece assembly 10 of FIG. 1 is provided. The ultrasonic handpiece 12 may comprise a proximal housing portion 14 and a distal housing portion 16, each of which may be configured to define a void. The proximal housing portion 14 and the distal housing portion 16 may be configured as two separate components and may be coupled together by a laser weld or similar coupling process. Alternatively, proximal housing portion 14 and the distal housing portion 16 may including corresponding coupling features configured to couple the proximal housing portion 14 and the distal housing portion 16 together. It is also contemplated that the proximal housing portion 14 and the distal housing portion 16 may be configured as a single unitary component.

A transducer 44 may be disposed in the void defined by the ultrasonic handpiece 12. The transducer 44 may comprise a plurality of driver elements 46, such as piezoelectric crystals arranged in a stacked configuration. The piezoelectric crystals 46 may expand and contract based on the varied application of electricity. The transducer 44 may comprise a tube 43 that defines a lumen 45 that extends from the proximal end to the distal end of the transducer 44 to create a fluid passageway through the transducer 44. The tube 43 may take the form of a post. The tube 43 may extend through the collinear longitudinal axes of the driver elements 46. A proximal end mass 41 may be located adjacent to the proximal face of the most proximally located driver element 46.

It is further contemplated that the transducer 44 may alternatively include a plurality of magnetostrictive elements.

A horn 40 may be at least partially disposed within the void defined by ultrasonic handpiece 12. The horn 40 may be coupled to the distal end of the transducer 44. The horn 40 may be constructed from a rigid steel alloy, titanium or similar material. In operation, as the transducer 44 expands and contracts, the horn 40 will oscillate. The horn 40 may be removably coupled to the transducer 44. For example, the proximal end of the horn 40 may comprise a threaded male coupler and the distal end of the transducer 44 may comprise a corresponding female threaded coupler. Alternatively, the transducer 44 and the horn 40 may be permanently coupled via a weld, adhesive, or similar bonding process. The horn 40 may be configured to define a second conduit 42 that is in fluid communication with the lumen 45 defined by the tube 43 of the transducer 44. Collectively, the lumen 45 through the transducer 44 and the second conduit 42 through the horn 40 form a portion of a continuous fluid passageway that extends from the distal end of the ultrasonic handpiece 12 to the proximal end of the ultrasonic handpiece 12. The ultrasonic surgical handpiece assembly 10 is constructed so that the driver elements 46 are compressed between the proximal end mass 41 and the horn 40.

The fluid passageway through the ultrasonic handpiece 12 may be utilized to provide irrigation fluid and/or a vacuum through the ultrasonic handpiece 12. The distal end of the horn 40 may further comprise a threaded coupler 38 that is configured to removably couple the ultrasonic tip 20 to ultrasonic handpiece 12 via the horn 40. While the threaded coupler 38 on the distal end of the horn 40 may comprise threads configured to engage corresponding threads on the ultrasonic tip 20, it is further contemplated that other coupling methods may be utilized. For example, the distal end of the horn 40 may comprise features that allow snap fit engagement with the ultrasonic tip 20.

The control console 13 of the ultrasonic surgical handpiece assembly 10 may be configured to source drive signals over the cable 30 to which the ultrasonic handpiece 12 is connected. In many but not all versions of ultrasonic surgical handpiece assembly 10, the ultrasonic handpiece 12 and cable 30 are assembled as a single unit. The drive signals are applied to the piezoelectric crystals 46. At any given instant, the same drive signal is applied to each of plurality of piezoelectric crystals 46. The application of the drive signals causes the piezoelectric crystals 46 to simultaneously and cyclically expand and contract. A stack of piezoelectric crystals 46 is often between 1 and 5 cm in length. The distance, the amplitude, of movement over a single expansion/contraction cycle of the piezoelectric crystals 46 may be between 1 and 10 microns. The horn 40 may be configured to amplify this movement. Consequently, the distal end of the horn 40 and, by extension, the ultrasonic tip 20, when moving from the fully contracted position to the fully extended position typically moves a maximum of 1000 microns and more often 500 microns or less. Some ultrasonic tips 20 are further designed to so that the longitudinal extension/retraction of the ultrasonic tip 20 may also induces a torsional movement in the cutting feature 34. When ultrasonic handpiece 12 is actuated to cause the cyclic movement of the ultrasonic tip 20, the cutting feature 34 is considered to be vibrating.

The control console 13 may also include a vacuum pump and controller, and an irrigation pump and a controller. The vacuum pump may be coupled to the ultrasonic surgical handpiece assembly 10 via aspiration line 27. The irrigation pump may be coupled to the ultrasonic handpiece assembly 10 via irrigation line 29. The control console 13 may have any of the features described in U.S. Patent Publication No. 2017/0071621 and 2018/0056328, which are hereby incorporated by reference in their entirety.

The ultrasonic handpiece 12 may also comprise a tube 58 that is at least partially disposed within the ultrasonic handpiece 12 and configured to define a lumen 59 through the ultrasonic handpiece 12 for irrigation and/or suction. The tube 58 defines an additional lumen 59 through the ultrasonic handpiece 12 to the passageway defined by the lumen 45 of the transducer 44 and the second conduit 42 of the horn 40. For example, the tube 58 may define an irrigation lumen 59 through the ultrasonic handpiece 12 and the lumen 45 through the transducer 44 and the second conduit 42 through horn 40 may define an aspiration lumen 45 through the ultrasonic handpiece 12. Alternatively, the tube 58 may define an aspiration passageway 59 through the ultrasonic handpiece 12 and the lumen 45 through the transducer 44 and the second conduit 42 through the horn 40 may define an irrigation passageway through the ultrasonic handpiece 12.

As described above, the irrigation and/or the aspiration passageways are disposed mostly within the ultrasonic handpiece 12 to provide ergonomic advantages by eliminating the one or more tubes typically attached to the exterior of the ultrasonic handpieces. It should be understood that while portions of the lines that define the aspiration passageway and/or the irrigation passageway from the proximal end of the ultrasonic surgical handpiece assembly 10 to the distal end of the passageway may be exposed, i.e., visible to a user during operation, there is no need for users to attach any irrigation lines or aspiration lines to the sides of the ultrasonic surgical handpiece assembly 10 during use. Instead, the irrigation lines 29 and aspiration lines 27, in certain embodiments, solely attach to the proximal end, even the rear face of the proximal end of the ultrasonic handpiece 12. In addition, in certain embodiments, during set-up of the ultrasonic surgical handpiece assembly 10, all of the aspiration and irrigation connections that the sleeve includes are sourced directly from the ultrasonic handpiece 12. In other words, there are no irrigation or aspiration lines that couple to a side of the sleeve 18. Thus, the ultrasonic handpiece 12 may include connections for both irrigation and aspiration.

Figure 4:
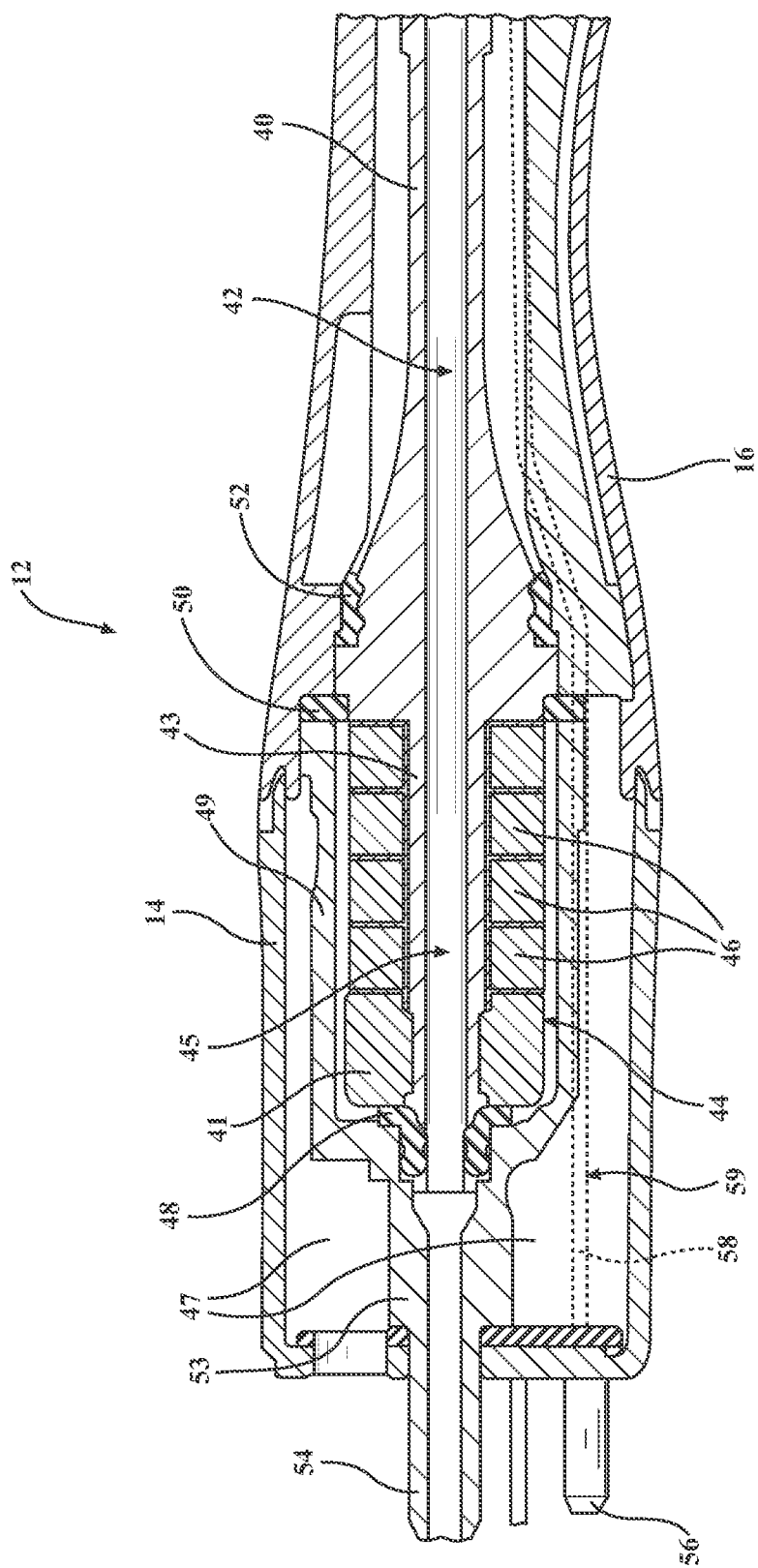
FIG. 4 is a zoomed (enhanced) sectional view of a rear housing portion of the ultrasonic handpiece of FIG. 3.

Referring to FIG. 4, a sectional view of a portion of the ultrasonic handpiece 12 is illustrated. As described above, the transducer 44 may comprise a distal end and a proximal end disposed within the void of ultrasonic handpiece 12. The transducer 44 may be configured to expand and contract along the longitudinal axis of the transducer 44. The lumen 45 through the transducer 44 comprises a distal portion and a proximal portion. The horn 40 may also be at least partially disposed within the ultrasonic handpiece 12.

The ultrasonic handpiece 12 may further comprise a barrier member 49 positioned within the void defined by the ultrasonic handpiece 12 and configured to define a cavity. The transducer 44 may be encased within the barrier member 49, such that the barrier member 49 may be configured to assist in mounting and isolating the transducer 44 within the ultrasonic handpiece 12. The barrier member 49 may not occupy the entirety of the void defined within the ultrasonic handpiece 12. Therefore, the ultrasonic handpiece 12 may further comprise a potting element 47 or material that is disposed within void defined by the ultrasonic handpiece 12. The potting element 47 may be disposed within the void defined by the ultrasonic handpiece 12 and exterior to the barrier member 49, such that the potting element 47 may occupy or fill the portion of the void within the handpiece 12 that is not occupied by the barrier member 49 or occluded by the barrier member 49. The potting element 47 may be configured to fix the position of the barrier member 49 within the void defined by the ultrasonic handpiece 12. The potting element 47 may also function as an insulator or dampener configured to prevent the transfer of thermal energy (i.e., heat) and mechanical energy (i.e., vibration) from the transducer 44 to the user's hand.

The barrier member 49 may further define a channel 53 extending in a generally proximal direction from the proximal end of the barrier member 49. The channel 53 forms a passageway between the proximal end of the ultrasonic handpiece 12 and the tube 43 that defines the lumen 45 through the transducer 44. The channel 53 may further comprise a coupling portion 54, such as a hose barb or similar fitting configured to create a friction fit, that extends proximally from the proximal end of the ultrasonic handpiece 12 and is configured to couple the channel 53 to the aspiration line 27 of the control console 13.

The transducer 44 may be partially mounted in the cavity defined by the barrier member 49 by a rear seal 48 positioned between said proximal end of the transducer 44 and an interior surface of the barrier member 49. The rear seal 48 may be configured to abut said proximal end of the transducer 44 and define a first aperture that is in fluid communication with the lumen 45 through the transducer 44. The rear seal 48 is positioned to help prevent moisture ingress to the volume that surrounds the transducer 44, in between the barrier member 49 and the exterior of the transducer 44. The rear seal 48 also functions to prevent moisture from entering between the exterior surface of the tube 43 and the interior surface of the transducer 44. The rear seal 48 may be formed from an elastomeric material that is resistant to heat and vibration degradation, including those materials that can withstand temperatures of an autoclave process.

The ultrasonic handpiece 12 may further comprise a front seal 52 disposed radially about an exterior surface of the horn 40 to prevent moisture ingress between an interior surface of the distal housing portion 16 and the horn 40. This is because the exterior surface of the horn 40 will be exposed to liquid during operation of the ultrasonic handpiece 12. The front seal 52 may further comprise a plurality of protrusions or bumps configured to facilitate engagement between the horn 40 and the distal housing portion 16 and prevent ingress of moisture into the void between the horn 40 and the distal housing portion 16 of the ultrasonic handpiece 12.

The ultrasonic handpiece 12 may further comprise a potting seal 50 positioned between and engaging both a distal end of the barrier member 49 and the proximal end of the horn 40. The potting seal 50 may also be configured to contact an interior surface of distal housing portion 16 of the ultrasonic handpiece 12 that is adjacent to the barrier member 49 and the proximal end of the horn 40. The potting seal 50 may be configured to abut the distal end of the barrier member 49 and define a second aperture for receiving the coupling feature of the horn 40. The potting seal 50 may be configured to prevent the potting element 47 from entering the barrier member 49 and contacting the transducer 44 during the potting process. Once the potting element 47 is in place, the potting element 47 in conjunction with the potting seal 50 helps to prevent moisture from entering between the barrier member 49 and the horn 40.

Figure 5:
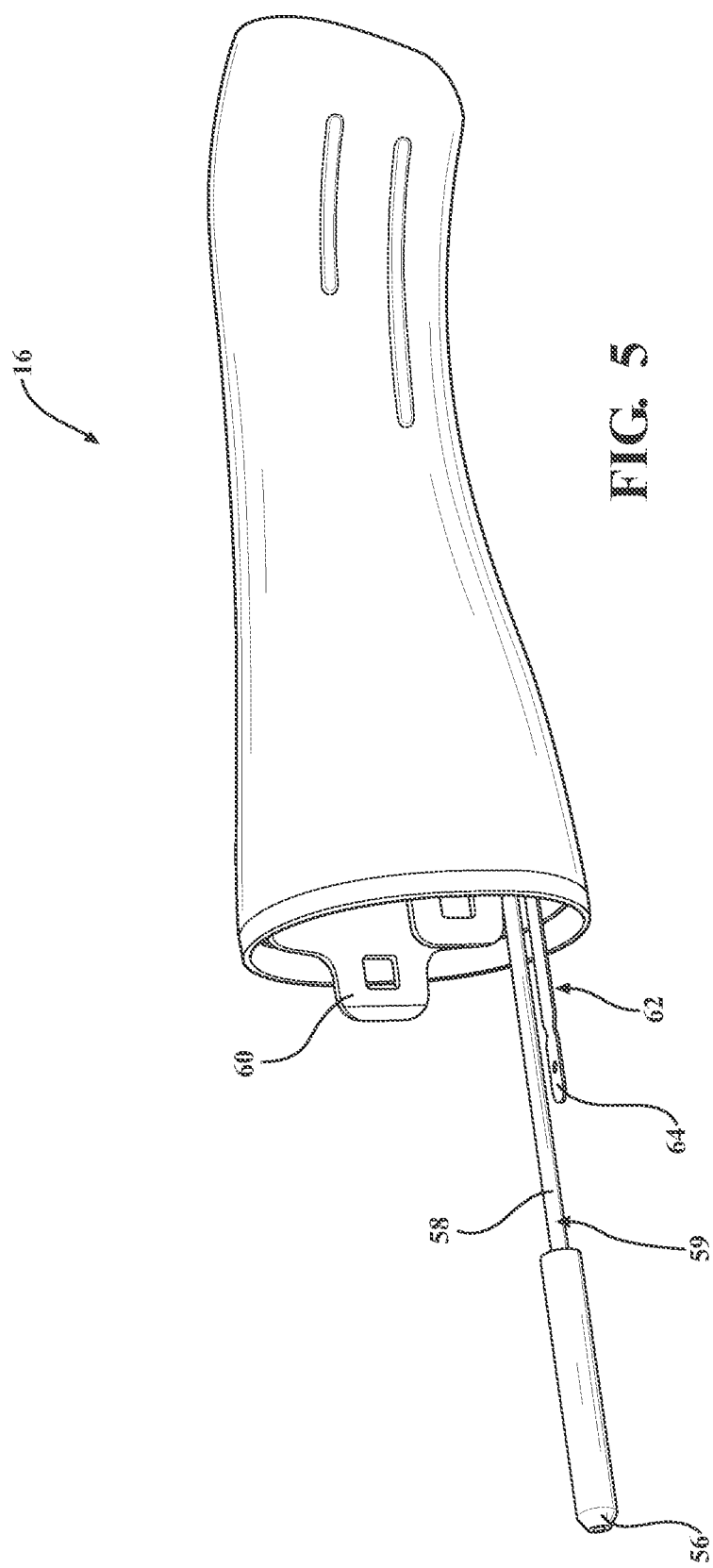
FIG. 5 is a perspective view of a front housing portion of the ultrasonic handpiece of FIG. 1.
Figure 6:
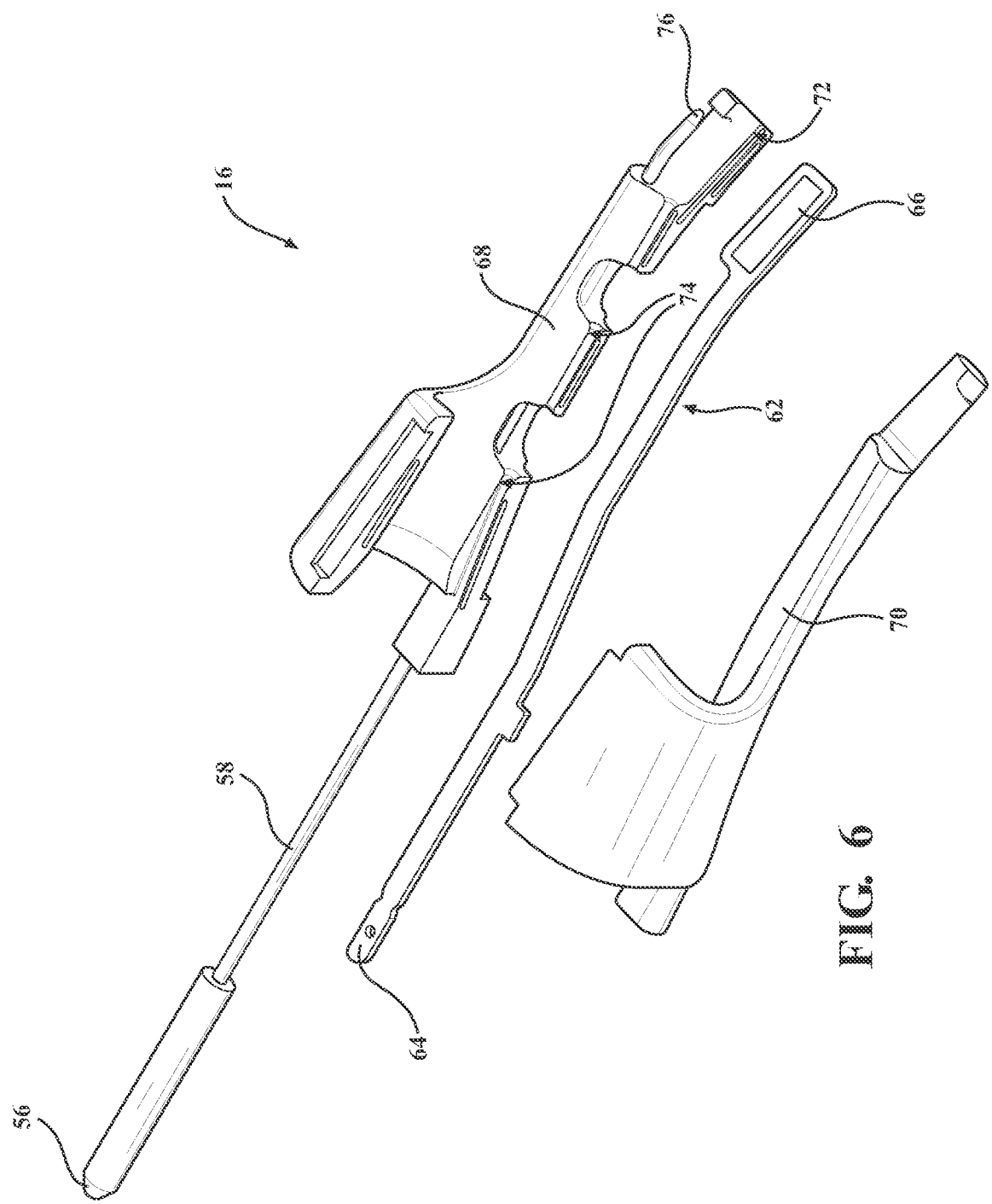
FIG. 6 is an exploded view of the front housing portion of FIG. 4.

Referring to FIGS. 5 and 6, an exemplary configuration of the distal housing portion 16 is illustrated. The distal housing portion 16 may comprise a coupling feature 60 configured to removably couple the distal housing portion 16 to a distal portion of the barrier member 49 that is disposed within the proximal housing portion 14. The coupling feature 60 may comprise a pair of tabs configured to create a snap and/or friction fit with a corresponding coupling feature of the barrier member 49. However, alternative coupling features are also contemplated, such as hooks or protrusions. The coupling feature 60 may assist in mounting and/or positioning the barrier member 49 within the void defined by the distal housing portion 16 and the proximal housing portion 14.

The distal housing portion 16 of the ultrasonic handpiece 12 may further comprise a flex circuit 62 that may be molded into the distal housing portion 16. The flex circuit 62 may be constructed from an electrically conductive material configured to transmit electrical signals between a distal region and proximal region of the flex circuit 62. The flex circuit 62 may comprise an attachment portion 64 positioned at the proximal region of the flex circuit 62 and configured to couple to a processor disposed within the ultrasonic handpiece 12 that is configured to communicate with the control console 13. Alternatively, the attachment portion 64 of the flex circuit 62 may be configured to couple to a wire, cable, or similar conductor that may couple to the control console 13 via the cable 30. The processor or wire may be configured to transport electrical signals between the flex circuit 62 and the control console 13 that may control the power supply, irrigation, and/or aspiration functions of the ultrasonic handpiece 12. The flex circuit 62 may also comprise a transceiver 66 positioned at the distal region of the flex circuit 62. As will be described below, the position of the transceiver 66 in the ultrasonic handpiece 12 should be tightly controlled in order to ensure that a corresponding coil of the sleeve 18 can be consistently read when the sleeve 18 is coupled to the ultrasonic handpiece 12.

Also illustrated in FIG. 5 is the tube 58 defining the lumen 59 described above, that is at least partially disposed within the ultrasonic handpiece 12. The tube 58 may be at least partially disposed within the distal housing portion 16 and the proximal housing portion 14. The tube 58 may further comprise a coupling feature 56, such as a hose barb or similar fitting configured to create a friction fit, positioned at proximal end of the tube 58 and configured to couple to the tube 58 to an irrigation line 29 that is routed from the control console 13 to the ultrasonic surgical handpiece assembly 10. The irrigation line 29 from the console 13 may be coupled to the ultrasonic handpiece 12 via the hose barb 56 to facilitate the flow of irrigation fluid through tube 58 within the ultrasonic handpiece 12 to the sleeve 18 and/or ultrasonic tip 20. In the configuration described above, the irrigation fluid may flow from the proximal end to the distal end of the ultrasonic handpiece 12 within the ultrasonic handpiece 12 or sleeve 18 eliminating the need for bulky irrigation lines coupled to the side of the ultrasonic handpiece 12 or the side of the sleeve 18. The routing of irrigation lines through the handpiece 12 enables this configuration. Thus, neither the sleeve, nor the ultrasonic handpiece includes an irrigation coupling part along the sides. Alternatively, in other configurations, the tube 58 may be coupled to an aspiration line 27 via the coupling feature 56. The aspiration line 27 may be utilized to draw a vacuum through the tube 58. The tube 58 may be in communication with the sleeve 18 and/or ultrasonic tip 20 to remove biological material and/or fluid from the surgical site.

Referring to FIG. 6, an exploded view of the distal housing portion 16 of the ultrasonic handpiece 12 is illustrated. The distal housing portion 16 may comprise a first half 68 and a second half 70 that are configured to be coupled together to form a portion of the distal housing portion 16. Each of the first half 68 and the second half 70 may be injection-molded from injection-molded plastic or similar lightweight and durable material. Furthermore, each of the first half 68 and the second half 70 may be molded to include a groove 74 or recessed portion that forms a channel in the distal housing portion 16 when the first half 68 and the second half 70 are coupled together. It is also contemplated that the groove 74 may only be formed in one of the first half 68 or the second half 70. The groove 74 may be configured to receive at least a portion of the flex circuit 62. The groove 74 may further comprise a cavity 72 at the distal end of the groove 74, wherein the cavity 72 is configured to receive the transceiver 66 at the distal region of the flex circuit 62. The cavity 72 may comprise larger dimensions than the groove 74 to accommodate the size of the transceiver 66 relative to the flex circuit 62 and the cavity 72 and the groove 74 may be contiguous. While the cavity 72 is illustrated as being positioned proximate the distal end of the distal housing portion 16, it is contemplated that the first and second halves 68, 70 may be configured wherein the flex circuit 62 and the transceiver 66 to be positioned at alternative locations. For example, the cavity 72 could be positioned closer to the proximal end of the distal housing portion 16. In yet another configuration, the first and second halves 68, 70 may be configured to be split along a horizontal axis, as opposed to along a vertical axis, such that the first half 68 is positioned superior to the second half 70. In this configuration, the groove 74 and the cavity 72 may be formed within the interface of the first and second halves 68, 70 such that the flex circuit 62 and transceiver 66 may be positioned on the right or left side of the distal housing portion 16.

The position of the cavity 72 should be tightly controlled in order to enable communication between the transceiver 66 and RFID tag 88 of the sleeve 18 (See FIG. 8). For example, the cavity 72 may be positioned within the distal housing portion 16 to reduce the distance between the transceiver 66 and the corresponding RFID tag 88 of the sleeve 18 when the sleeve 18 and ultrasonic handpiece 12 are coupled together. The cavity 72 is positioned to ensure that the plane defined by the transceiver 66 is positioned substantially parallel to the plane defined by the RFID tag 88 of the sleeve 18.

As described above, the flex circuit 62 may comprise a transceiver 66 positioned at the distal end of the flex circuit 62. The transceiver 66 may comprise an antenna configured to send out a signal to a corresponding RFID tag associated with the sleeve 18 and receive a response. The flex circuit 62 may be disposed at least partially within the groove 74 of the distal housing portion 16 when the first half 68 and the second half 70 are coupled together. The flex circuit 62 may generally be formed as a thin strip of ribbon including internal copper elements, such as wiring. The configuration and structure of the flex circuit 62 may result in the flex circuit 62 being frail or easily damaged. This can make working with and or installing the flex circuit into the distal housing portion 16 difficult. For example, one needs to handle the flex circuit in a manner that protects against crushing or breaking. One also wants to be careful to avoid operations that may cause the layers of the flex circuit 62 to delaminate. Therefore, the groove 74 formed in the distal housing portion 16 should avoid sharp bends or turns and seek to provide a smooth transition along the length of the grove 74. During the assembly process, the flex circuit 62 is positioned within the groove 74 and the transceiver 66 within the cavity 72 prior to coupling the first half 68 and the second half 70 of the distal housing portion 16, such that the position of the transceiver 66 may be fixed within the distal housing portion 16. It should be appreciated that the transducer need not always be at the distal end of the flex circuit.

Once the first half 68 and the second half 70 of the distal housing portion 16 have been mechanically fit together such that the position of the transceiver 66 is fixed, the distal housing portion 16 may be over-molded with autoclaveable plastic to produce the final configuration of distal housing portion 16 illustrated in the FIG. 5. Over-molding the flex circuit 62 and transceiver 66 within the distal housing portion 16 of the ultrasonic handpiece 12 with an autoclaveable plastic serves to protect the flex circuit 62 from being damaged by heat during the autoclave process utilized to sterilize the ultrasonic handpiece 12. Furthermore, the use of autoclaveable plastic as opposed to plastic having a lower melting point than 150 degrees Celsius, allows the distal housing portion 16 to be repeatedly subject to autoclave sterilization processes without experiencing significant degradation. Finally, by positioning the flex circuit 62 within the groove 74 of the first and second halves 68, 70 before overmolding with the autoclaveable plastic, the flex circuit 62 is sufficiently insulated by the first and second halves 68, 70 from the thermal energy of the melted autoclaveable plastic such that the flex circuit 62 does not delaminate during the overmolding process. The result of the process described above can be shown in the device illustrated in FIGS. 5 and 8. Autoclaveable plastic should be understood as polymers having a melting point greater than 150 degrees Celsius.

While the process of positioning the flex circuit 62 is described with respect to the two halves 68, 70 of the distal housing portion 16, it should be appreciated that a similar process can be used with any suitable medical device housing where it is important to precisely position a portion of a flex circuit 62, including those medical device housings that do not include two distinct halves.

While not illustrated, the ultrasonic handpiece 12 also includes a memory. The memory may contain data describing the characteristics of the ultrasonic handpiece 12. Memory may take the form of an EPROM, an EEPROM or be included with the RFID tag 88 described above. The memory, in addition to containing data capable of being read, is able to store data written to the memory after manufacture of the ultrasonic handpiece 12. Ancillary components not illustrated are mounted to the handpiece to facilitate the reading of data from and the writing of data to the memory. These components consist of one or more of the following: conductors; exposed contacts/contact pins; a coil/antenna; or an isolation circuit.

Figure 7:
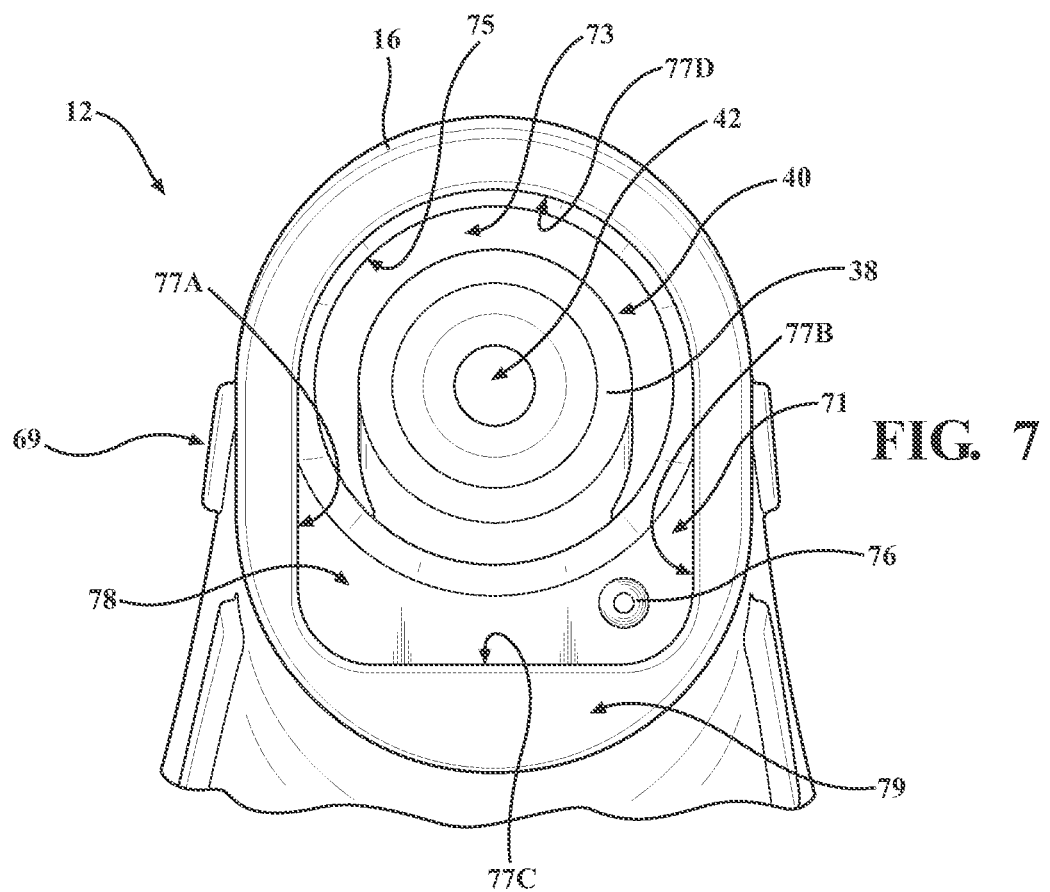
FIG. 7 is a front view of the ultrasonic handpiece of FIG. 6.
Figure 9:
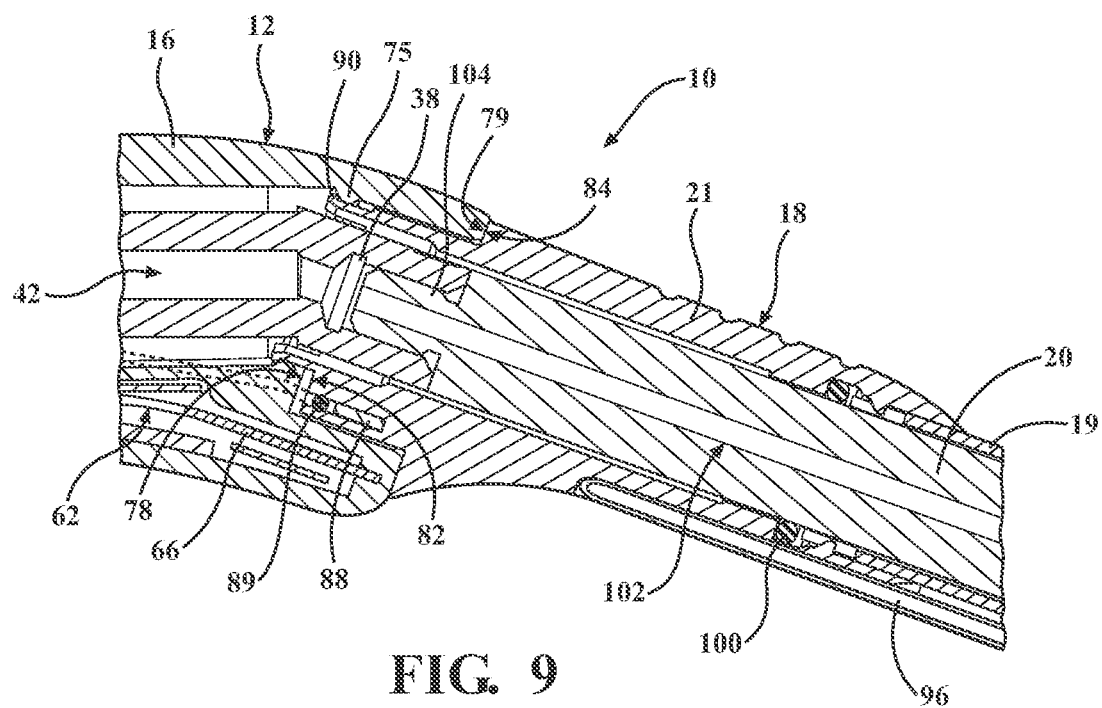
FIG. 9 is a zoomed (enhanced) sectional view of the front housing portion of the ultrasonic handpiece coupled to the irrigation sleeve.

Referring to FIGS. 7-9, an exemplary configuration of the interface between the distal housing portion 16 and the sleeve 18 and/or ultrasonic tip 20 is illustrated. FIG. 7 illustrates a front view of an example configuration of the distal end of the distal housing portion 16 described above. This may also be referred to as the distal end of the ultrasonic handpiece 12. The distal end of the ultrasonic handpiece 12 may comprise an attachment region 69 configured to serve as the interface between the ultrasonic handpiece 12 and the sleeve 18 and the ultrasonic tip 20. The attachment region 69 may comprise a recess 71 defined by a proximal surface 78 and a distal surface 79 that are connected by a plurality of walls 77 extending perpendicular to the proximal surface 78 and the distal surface 79. The proximal surface 78 may comprise an aperture 73 including a coupling feature 75 at the perimeter of the aperture 73 (See FIG. 9). The coupling feature 75 may comprise a tab, lip, or similar snap fit coupling mechanism.

The distal end of the horn 40 may be configured to partially extend through the aperture 73 defined in the proximal surface 78, wherein at least a portion of the horn 40 and the threaded coupler 38 are disposed within the recess 71 at the distal end of the ultrasonic handpiece 12. The second conduit 42 that extends through the horn 40 may similarly open to the recess 71.

The proximal surface 78 may further comprise an irrigation coupler 76 positioned at the distal end of the tube 58 defining the lumen 59 through the ultrasonic handpiece 12. The irrigation coupler 76 may comprise a fitting, hose barb, or similar coupling member for coupling the distal end of the tube 58 to a corresponding irrigation line 29 of the sleeve 18. The irrigation coupler 76 may be configured to be in fluid communication with the lumen 59 disposed within the ultrasonic handpiece 12 to provide irrigation fluid to the sleeve 18. The irrigation coupler 76 may serve as an inlet or an outlet to transport material and/or fluid between the ultrasonic handpiece 12 and sleeve 18.

Referring to FIG. 8, a partially exploded view of the interface between the distal end of the ultrasonic handpiece 12 and the sleeve 18 is illustrated. The sleeve 18 may comprise a hub 21 positioned at a proximal end of the sleeve 18 and a sleeve body 19 that extends distally from the hub 21. The sleeve 18 may comprise a lumen 98 defined by the hub 21 and sleeve body 19 that extends the length of sleeve 18 and is configured to surround at least a portion of the ultrasonic tip 20 when coupled to the ultrasonic handpiece 12. The hub 21 may comprise a protrusion 80 that extends proximally from a distal surface 84 of the hub 21 and terminates at a proximal surface 82. The proximal surface 82 of the protrusion 80 may be oriented to be generally parallel to the distal surface 84. The shape of the protrusion 80 may be defined by a plurality of external circumferential surfaces 81 or wall members that extend between the distal surface 84 and the proximal surface 82 and are configured to define the outer perimeter of the protrusion 80. The external circumferential surfaces 81 may be oriented to be generally perpendicular to the proximal surface 82 and/or the distal surface 84. It should be appreciated the shape of the protrusion 80 is positioned to fit closely within the recess 71, such that the external circumferential surfaces 81 of the protrusion 80 engage the walls 77 of the recess 71.

However, while not illustrated in the figures, it is further contemplated that the external circumferential surfaces 81 of the protrusion 80 may be oriented at an angle other than 90 degrees relative to the proximal surface 82 and/or the distal surface 84 in order to create a tapered protrusion 80. For example, the area defined by the external circumferential surfaces 81 of the protrusion 80 proximate the distal surface 84 may be greater than the area of the proximal surface 82.

The hub 21 may further comprise a fitting 94 extending from the proximal surface 82 of the protrusion 80. The fitting 94 may be configured to couple to the corresponding fitting 76 of the ultrasonic handpiece 12. The fitting 94 of the sleeve 18 and corresponding fitting 76 of the ultrasonic handpiece 12 may be configured to facilitate the exchange of fluid between the sleeve 18 and the ultrasonic handpiece 12. In particular, the fitting 76 is sized to fit within the fitting 94 when the sleeve 18 is coupled to the ultrasonic handpiece 12. For example, irrigation fluid from the ultrasonic handpiece 12 may be dispersed to the sleeve 18 through the connection of the fitting 94 to the fitting 76. This eliminates the need to connect the sleeve to an irrigation line that is separate from the ultrasonic handpiece 12, e.g., such as an irrigation line that connects to a side of the sleeve 18. Alternatively, a vacuum may be applied to the ultrasonic handpiece 12 configured to aspirate material from the sleeve 18 through the fittings 94 and 76 when coupled in an alternative configuration.

The sleeve 18 may further comprise a conduit 96 formed in the sleeve body 19 that runs adjacent to the lumen 98 of the sleeve 18. The fitting 94 may be coupled to the proximal end of the conduit 96. The conduit 96 may be configured to channel irrigation fluid through the sleeve 18 separate from the lumen 98 of the sleeve 18. The conduit 96 may be routed in various ways through the sleeve 18.

The hub 21 may further comprise a cavity 86 in the protrusion 80 that that includes an opening in the proximal surface 82 of the protrusion 80. The cavity 86 may be configured to at least partially enclose a tag 88, antenna, transceiver, or similar wireless communication device that is configured to communicate with the transceiver 66 disposed in the distal housing portion 16 of the ultrasonic handpiece 12. For example, the tag 88 may comprise an RFID tag 88 that may be inserted and/or disposed within the cavity 86. While the figures illustrate the cavity 86 and RFID tag 88 as being positioned generally near the proximate end of the sleeve 18, it should be understood that the cavity 86 and RFID tag 88 may be positioned at other locations on or within the sleeve 18. For example, the RFID tag 88 may be positioned within one of the other external circumferential surfaces 81A, 81B, or 81D of the protrusion 80. Alternatively, the cavity 86 and RFID tag 88 may be positioned within the distal surface 84 of the hub 21. The RFID tag 88 may include a memory unit that stores data and/or information related to one or more properties or characteristics related to the sleeve 18 and ultrasonic tip 20. For example, the RFID tag 88 may comprise information identifying the type of cutting feature 34 disposed on the distal end of the ultrasonic tip 20. The RFID tag 88 may also comprise information identifying the type of sleeve 18. This information may be communicated to the ultrasonic handpiece 12 and subsequently the console 13 so that the console 13 may modify power settings, irrigation settings, aspiration settings, and/or other settings intended to optimize the efficiency of the cutting feature 34 of the ultrasonic tip 20. This may include control parameters that are not specific to the power and tip to the ultrasonic handpiece 12 compatibility settings. The RFID tag 88 may also be used to prevent customers from reusing ultrasonic tip 20 and/or sleeve 18 as part of a sterilization standard or procedure. For example, the ultrasonic tip 20 and sleeve 18 may be configured as a single use component that is not intended to be sterilized and reused. The RFID tag 88 also includes a coil 89. The shape of the protrusion 80 and the recess 71 are arranged such that the plane defined by the coil 89 of the RFID tag 88 is generally parallel to the plane defined by the transceiver 66.

The RFID tag 88 in the sleeve 18 may be understood as the tip memory. The ultrasonic tip 20 and the sleeve 18 are typically packaged together in a kit. The data contained in the RFID tag 88 may be used control actuation of the ultrasonic tip 20. The coil 89 embedded in the sleeve 18 is coupled to memory unit of the RFID tag 88. As described above, the RFID tag 88 may be used to prevent customers from reusing ultrasonic tip 20 and/or sleeve 18. In combination with the memory unit, the RFID tag 88 may be further configured to track and/or count the number of uses and limit the number of times a tip is used. For example, the RFID tag 88 may be configured to store on the memory unit the number and/or amount of time the ultrasonic tip 20 and sleeve 18 are operated. The RFID tag 88 and memory unit may be configured to prevent actuation of the tip a define number of uses. The defined number of uses may be passed on wear and effectiveness of the ultrasonic tip 20 and/or sleeve 18, in order to prevent or predict failure.

As illustrated in FIG. 9, the tag 88 may be secured in the cavity 86 by a pin 89. The pin 89 may comprise a plastic or alloy material and be configured to create a friction fit within the opening of the cavity 86 to secure the RFID tag 88 within the cavity 86 and protect it from being damaged. Alternatively, the pin 89 may comprise a seal such as an elastomeric O-ring. In yet another configuration, the pin 89 may comprise an epoxy, glue, sealant, or similar compound configured to secure the tag 88 within the cavity 86 and protect the tag from damage. It is further contemplated that the RFID tag 88 may be injection molded or heat staked into the sleeve 18. The RFID may also take other forms of tags.

The protrusion 80 may be configured in a complementary shape to the one defined by the recess 71 at the distal end of the ultrasonic handpiece 12, wherein the protrusion 80 is configured to be disposed within the recess 71 when the sleeve 18 is coupled to the ultrasonic handpiece 12. Furthermore, the shape of the recess 71 and the protrusion 80 may be configured to align the sleeve 18 relative to the ultrasonic handpiece 12, as well as prevent rotational movement of the sleeve 18 relative to the ultrasonic handpiece 12. For example, as illustrated in FIG. 8, the recess 71 of the ultrasonic handpiece 12 comprises a plurality of walls 77 that define the perimeter of the recess 71. In the example configuration of the recess 71 illustrated in FIGS. 7-8, the walls 77A, 77B, 77C, and 77D define a doghouse-like shape, wherein you have two opposing walls 77A, 77B, that are generally parallel to one another. The two opposing walls 77A, 77B are connected by a third wall 77C that is generally perpendicular to the two opposing walls 77A, 77B. A fourth wall 77D, that connects the two opposing walls 77A, 77B opposite the third wall 77C, may comprise a generally arch-like shape. The plurality of external circumferential surfaces 81A, 81B, 81C, and 81D that define the outer perimeter of the protrusion 80 may then be configured to define a doghouse-like shape that corresponds to the shape of the recess 71. While not illustrated in the figures, it is contemplated that the walls 77A, 77B, 77C, and 77D of the recess 71 and the corresponding external circumferential surfaces 81A, 81B, 81C, and 81D of the protrusion 80 may be configured to define alternative shapes. For example, the walls 77 and external circumferential surfaces 81 may define a rectangular shape, a star shape, an oval shape, a triangular shape or other similar shape. While the protrusion 80 and the recess 71 illustrated in the figures include complementary shapes, it is further also contemplated that the protrusion 80 and the recess 71 may have slightly different shapes, so long as the protrusion 80 may be disposed within the recess 71. For example, the protrusion 80 on the sleeve 18 may be configured to comprise several more external circumferential surfaces 81 to the protrusion by creating a chamfer between 81C and 81A and/or 81B and it would still insert and function in the ultrasonic handpiece 12.

The shape of the protrusion 80 and the recess 71 may further be configured to orient the tag 88 that is disposed in the cavity 86 of the hub 21 relative to the transceiver 66 disposed in the distal housing portion 16 of the ultrasonic handpiece 12. Utilizing the shape of the protrusion 80 and the recess 71 to orient the tag 88 relative to the transceiver 66 can improve the reliable establishment of communication between the tag 88 relative and the transceiver 66. For example, as illustrated in FIG. 9, the tag 88 and the transceiver 66 are positioned such that the tag 88 and the transceiver 88 at least partially overlap in an axial sense when the sleeve 18 is coupled to the ultrasonic handpiece 12. Furthermore, the cavity 86 in the hub 21 and the cavity 72 in the distal housing portion 16 of the ultrasonic handpiece 12 may be oriented such that a first longitudinal axis of the tag 88 and a second longitudinal axis of transceiver 66 are generally parallel to one another. The protrusion 80 and the distal housing portion 16 may further be configured to reduce the distance between the cavity 86 in the hub 21 and the cavity 72 in the distal housing portion 16 to further improve communication between the tag 88 and the transceiver 66.

The hub 21 may further comprise a plurality of retention fingers 90 that extend distally from the proximal surface 82 of the protrusion 80. The plurality of retention fingers 90 may be spaced about the perimeter of the lumen 98 defined in the proximal surface 82. The plurality of retention fingers 90 may further comprise a tab 92, bump, or protrusion configured to engage the coupling feature 75 at the perimeter of the aperture 73 in the proximal surface 78 of the recess 71 in the ultrasonic handpiece 12. The tab 92 of each of the plurality of retention fingers 90 may engage the coupling feature 75 of the recess 71 to create a snap-fit and/or friction fit to removably couple the sleeve 18 to the ultrasonic handpiece 12. The plurality of retention fingers 92 may comprise a very compliant material like a silicone rubber, or a metal material such as a leaf spring. While not illustrated in the figures, it is contemplated that the sleeve 18 may be coupled to the ultrasonic handpiece 12 in a number of other ways. For example, the hub 21 hub may be configured without and retention fingers 90, and the irrigation coupler 76 of the ultrasonic handpiece 12 may be mated with the irrigation fitting 94 of the sleeve 18 to form the primary retention mechanism. In yet another configuration, the protrusion 80 may comprise a compliant material, which contains the RFID tag 88 despised within a slit in the material, and the protrusion 80 may create an interference fit with the cavity 71.

Referring to FIG. 9, a sectional view of an example configuration of the interface between the distal housing portion 16 of the ultrasonic handpiece 12 and the sleeve 18 and ultrasonic tip 20 is illustrated. As illustrated in FIG. 9, the distal surface 79 of the distal housing portion 16 may abut the distal surface 84 of the protrusion 80 when the sleeve 18 is coupled to the ultrasonic handpiece 12. This may assist in forming a stable connection between the sleeve 18 to the ultrasonic handpiece 12. Similarly, the proximal surface 78 of the distal housing portion 16 may abut the proximal surface 82 of the protrusion 80 when the protrusion 80 is disposed within the recess 71 to couple the sleeve 18 to the ultrasonic handpiece 12. However, it is also possible that there may be a gap between the proximal surface 78 of the distal housing portion 16 and the proximal surface 82 of the protrusion 80 when the distal surface 79 of the distal housing portion 16 abuts the distal surface 84 of the protrusion 80.

In operation, the method of coupling the sleeve 18 to the ultrasonic handpiece 12 may comprise providing the ultrasonic handpiece 12 described above, wherein the ultrasonic handpiece 12 includes the irrigation tube 58 configured to communicate irrigation fluid through the ultrasonic handpiece 12. The ultrasonic handpiece 12 may also include the attachment portion 69 positioned proximate the distal end of the ultrasonic handpiece 12. The attachment portion 69 may comprise the recess 71 describes above, wherein the recess is defined by a plurality of side walls 77 configured to define a void, such as an asymmetric void. The attachment region 69 may also comprise an aperture or similar attachment element.

The method of coupling the sleeve 18 to the ultrasonic handpiece 12 may further comprise providing the sleeve 18 described above, wherein the sleeve 18 comprises the hub 21 that includes a proximal surface 82 and a distal surface 84. The proximal surface 82 may optionally comprise one or more retention fingers 90 and be configured to define an asymmetrical protrusion 80 extending proximally from the distal surface 84. The protrusion 80 may be sized to be inserted within the recess 71 of the ultrasonic handpiece 12.

The method of coupling the sleeve 18 to the ultrasonic handpiece 12 may further comprise coupling the ultrasonic handpiece 12 to the sleeve 18 by inserting the asymmetrical protrusion 80 into the asymmetrical void defined by the attachment portion 69 such that the one or more retention fingers 90 engage the perimeter of the aperture in the distal housing portion 16 to create an interference fit between the sleeve 18 to the ultrasonic handpiece. As the asymmetrical protrusion 80 is inserted into the asymmetrical void defined by the attachment portion 69, the irrigation coupler 76 of the ultrasonic handpiece 12 may be mated with the irrigation fitting 94 of the sleeve 18 to form an irrigation passageway between the ultrasonic handpiece 12 and the sleeve 18 without separately connecting an irrigation line to the irrigation sleeve 18. Thus, the irrigation and the aspiration lines may be coupled to the sleeve and the sleeve may be coupled to the ultrasonic handpiece with a single step—inserting the protrusion of the sleeve into the recess of the ultrasonic handpiece.

The method of coupling the sleeve 18 to the ultrasonic handpiece 12 may further comprise the step of providing the ultrasonic tip 20 described above, wherein the ultrasonic tip 20 comprises a threaded coupler 104 at the distal end of the ultrasonic tip 20 configured to removably secure the ultrasonic tip 20 to the threaded coupler 38 of the ultrasonic handpiece 12. The ultrasonic tip 20 may further comprise a cutting feature 34 at the distal end of the ultrasonic tip 20. The method may then comprise coupling the ultrasonic tip 20 to the ultrasonic handpiece 12 prior to the step of coupling the ultrasonic handpiece 12 to the irrigation sleeve 18.

The method of coupling the sleeve 18 to the ultrasonic handpiece 12 may further comprise the step of inserting the first irrigation coupler 76 on a distal end of the irrigation conduit or tube 58 of the ultrasonic handpiece 12 into a corresponding irrigation fitting 94 on the irrigation sleeve 18 as the asymmetrical protrusion 80 is inserted into the asymmetrical void defined in the attachment portion 69, wherein the irrigation fitting 94 is in fluid communication with the conduit 96 of the sleeve 18 and is configured to provide irrigation fluid to the ultrasonic tip 20.

Figure 10:
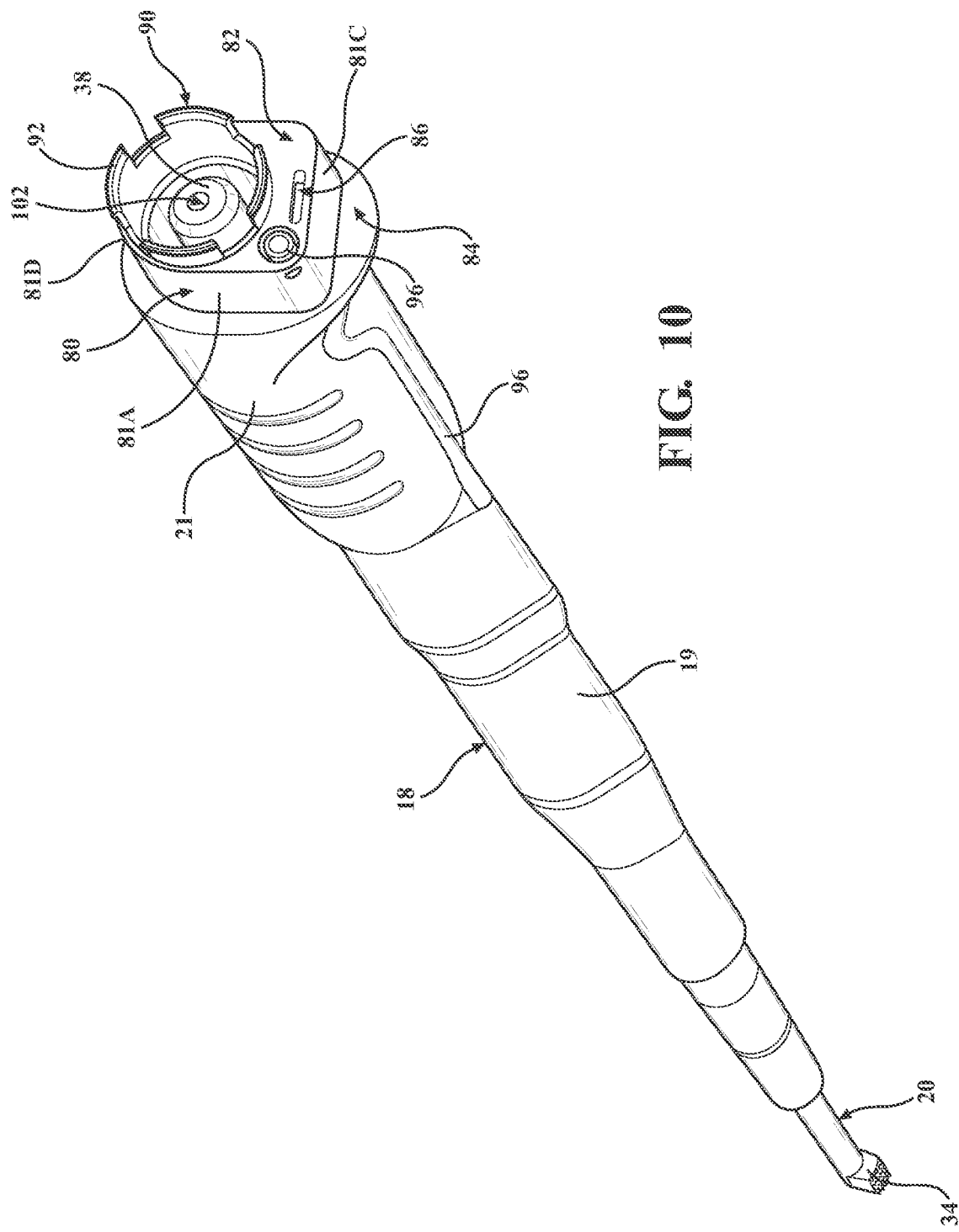
FIG. 10 is a perspective view of the irrigation sleeve and the ultrasonic tip of the ultrasonic surgical handpiece assembly FIG. 1, for use with the ultrasonic handpiece.
Figure 12:
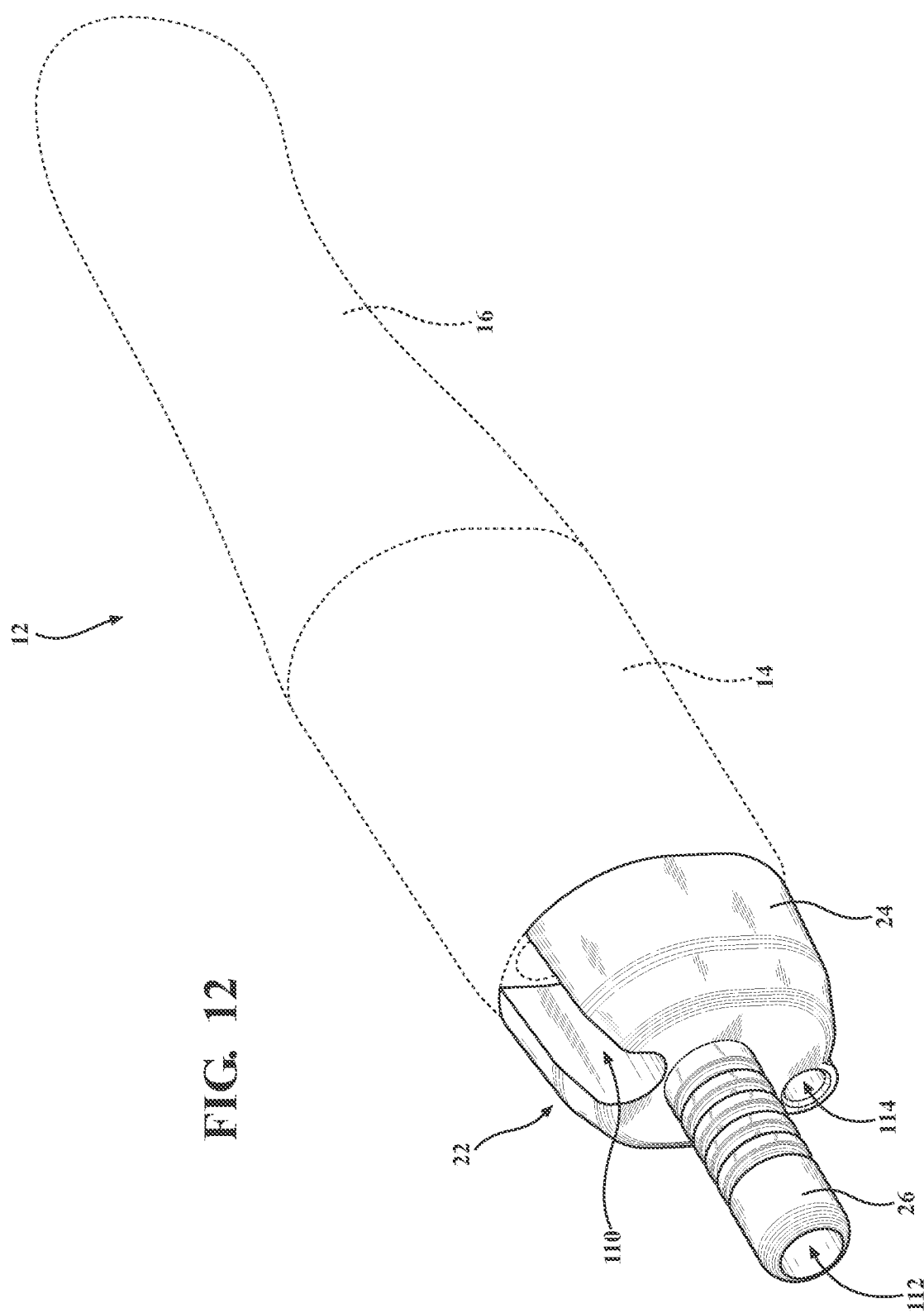
FIG. 12 is a perspective view of an example configuration of a tubing connector for use with the ultrasonic surgical handpiece assembly FIG. 1, including the ultrasonic handpiece shown in phantom.
Figure 13:
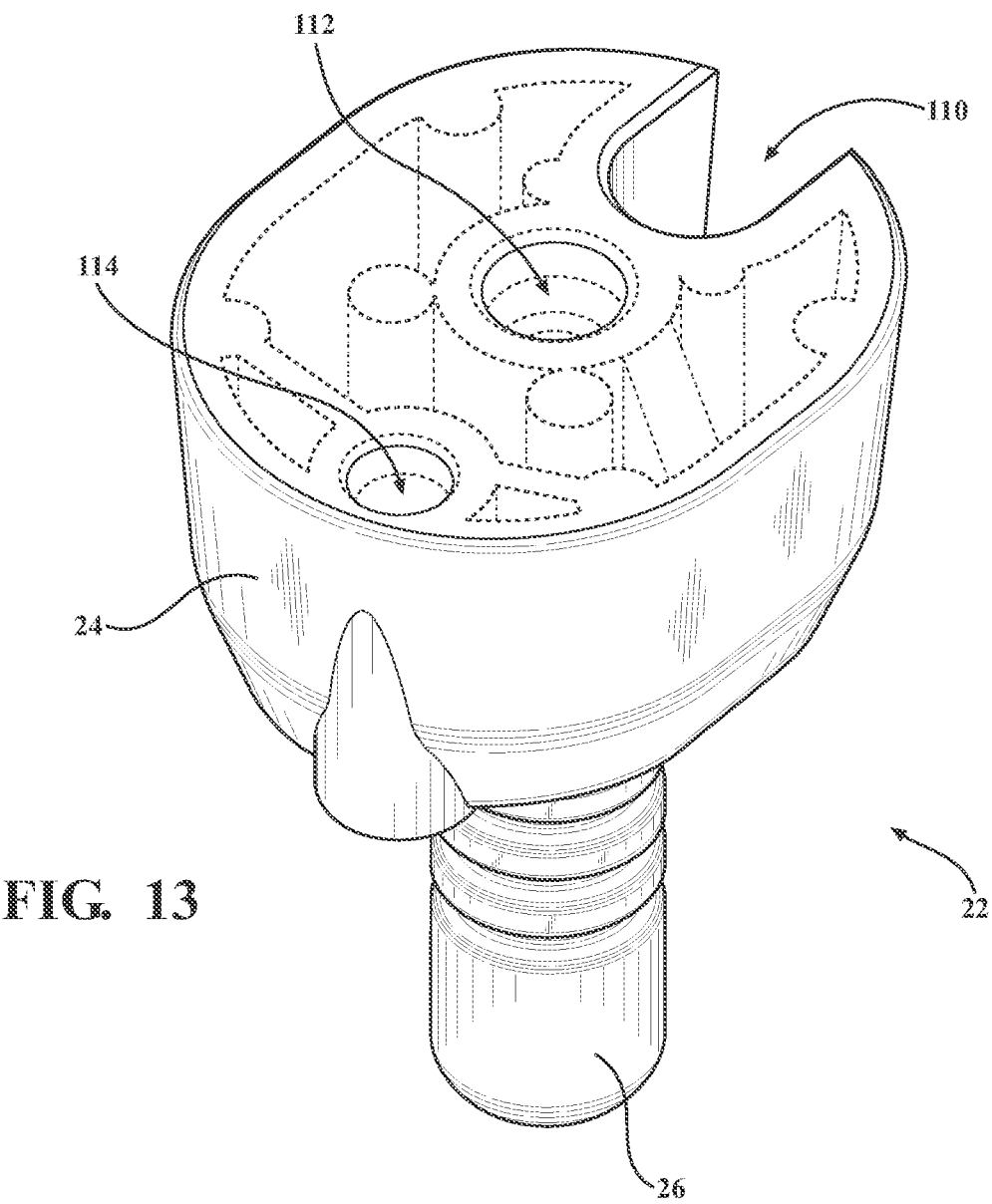
FIG. 13 is a first perspective view of the tubing connector of FIG. 12.
Figure 16:
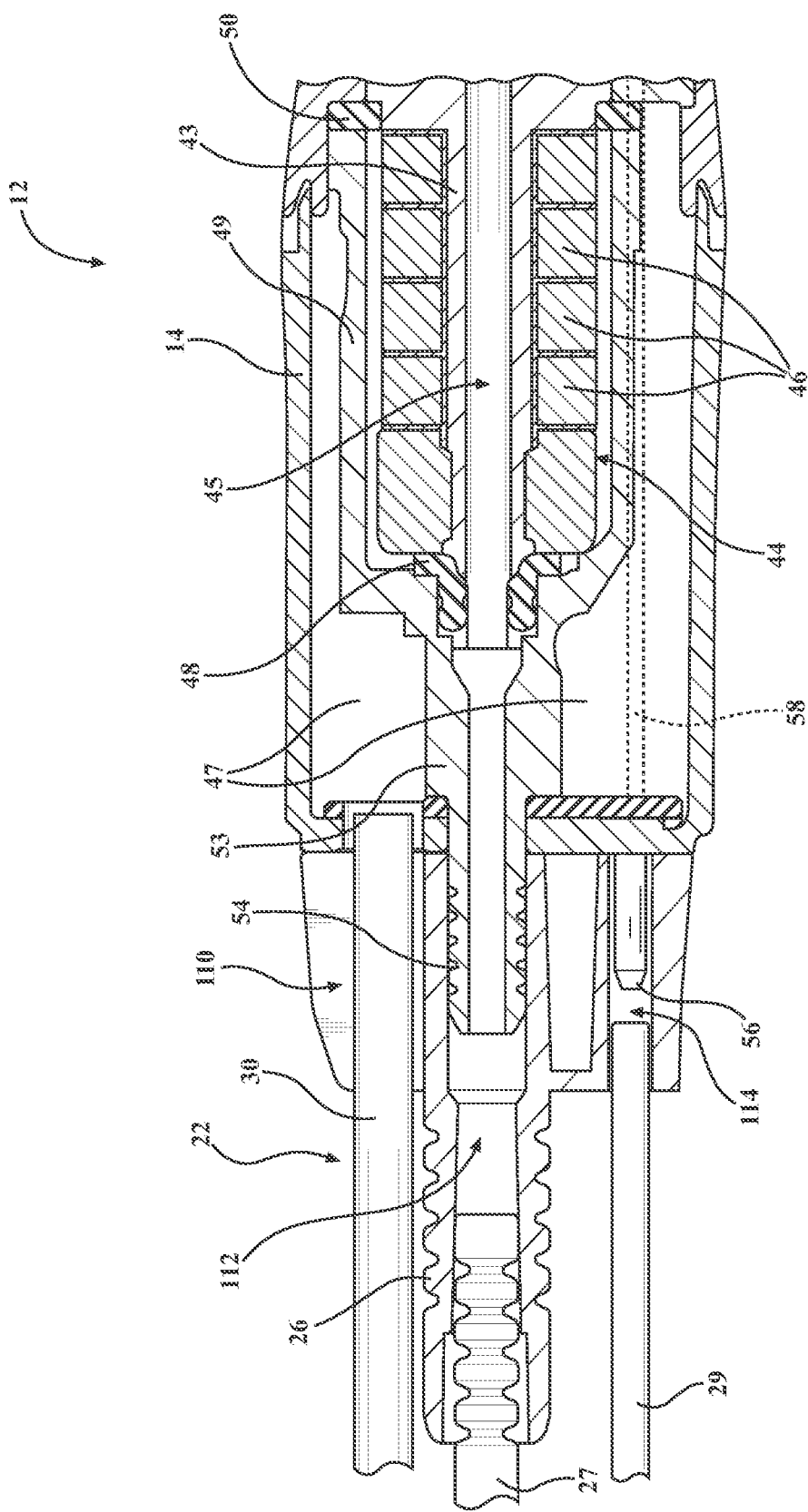
FIG. 16 is a cut-away sectional view of the tubing connector of FIG. 12 coupled to an ultrasonic handpiece with power, aspiration, and irrigation lines extending therefrom.

Referring to FIGS. 10, 11A, and 11B, an example configuration of the ultrasonic tip 20 disposed within the sleeve 18 is illustrated. Referring to FIG. 11B, a sectional view of the ultrasonic tip 20 disposed within the sleeve 18 is illustrated. As described above, the sleeve 18 may comprise the conduit 96 formed in the sleeve body 19 and runs adjacent to the lumen 98 of the sleeve 18. The distal end of the conduit 96 may terminate at an aperture 108 or nozzle positioned on an interior surface of the lumen 98. The aperture 108 may configured to direct fluid radially inward toward the center of the lumen 98. The fluid may then be applied to an exterior surface of the ultrasonic tip 20 and/or directed toward the distal end of the sleeve 18, wherein the fluid may exit the lumen 98 and be applied to the surgical site.

The sleeve 18 may further comprise a seal 100, such as O-ring, disposed within the lumen 98 and configured to contact a portion of the ultrasonic tip 20 when the sleeve 18 is coupled to the ultrasonic handpiece 12 and the ultrasonic tip 20 is coupled to the ultrasonic handpiece 12. The seal 100 may be configured to create a fluid seal between the interior surface of the lumen 98 and the exterior surface of the ultrasonic tip 20. For example, the seal 100 may be configured to prevent fluid that is between the interior surface of the lumen 98 and the exterior surface of the ultrasonic tip 20 distal of the seal 100 from flowing proximal of the seal 100.

The ultrasonic tip 20 may comprise a distal end and a proximal end. The ultrasonic tip 20 may include a cutting feature 34 at the distal end of ultrasonic tip 20 and a coupling feature 104, positioned at the proximate end. The coupling feature 104 may be configured to engage the threaded coupler 38 of the horn 40 to removably couple the ultrasonic tip 20 to the ultrasonic handpiece 12. It should be understood that the coupling feature 104 of the ultrasonic tip 20 should be configured to engage the threaded coupler 38 of the horn 40. Thus, if a coupling arrangement other than complementary threads is utilized, the coupling features 104, 38 of the ultrasonic tip 20 and the horn 40 are suitable to engage one another.

The ultrasonic tip 20 may be configured to define a lumen 102 that extends from the proximal end to the distal end of the ultrasonic tip 20. The lumen 102 may be configured to be in fluid communication with the fluid passageway through the ultrasonic handpiece 12 that is defined by the conduit 42 of the horn 40 and the lumen 45 of the transducer 44 when the ultrasonic tip 20 is coupled to the ultrasonic handpiece 12. The lumen 102 may be configured to provide irrigation and/or suction at the surgical site based on the system that is coupled to the fluid passageway through the ultrasonic handpiece 12 that is defined by the conduit 42 of the horn 40 and the lumen 45 of the transducer 44. For example, if an irrigation system is coupled to the fluid passageway through the ultrasonic handpiece 12 that is defined by the conduit 42 of the horn 40 and the lumen 45 of the transducer 44, the lumen 102 may be configured to provide irrigation fluid to the surgical site proximate the cutting feature 34. Alternatively, if an aspiration system is coupled to the fluid passageway through the ultrasonic handpiece 12 that is defined by the conduit 42 of the horn 40 and the lumen 45 of the transducer 44, the lumen 102 may configured to remove fluid and/or material from the surgical site proximate the cutting feature 34.

The ultrasonic tip 20 may also comprise an aperture 106 that is configured to be in fluid communication with the lumen 102. The aperture 106 may be positioned between the proximal end and distal end of the ultrasonic tip 20 such that the aperture 106 is distal of the seal 100 of the sleeve 18 when the ultrasonic tip 20 is disposed within the lumen 98 of the sleeve 18. Furthermore, the aperture 106 may positioned on the ultrasonic tip 20 such that the aperture 106 is surrounded by the sleeve 18 when the ultrasonic tip 20 is disposed within the lumen 98 of the sleeve 18. For example, the aperture 106 may be positioned on the ultrasonic tip 20 so that the aperture 106 is proximal of the distal end of the sleeve 18 when the ultrasonic tip 20 is disposed within the lumen 98 of the sleeve 18.

The ultrasonic tip 20 may further comprise a resonator 105 positioned between the proximal end and the distal end of the ultrasonic tip 20. This The resonator 105 may be configured to translate the longitudinal vibration transmitted from the transducer 44 to the ultrasonic tip 20 via the mechanical connection created by the horn 40 into longitudinal and torsional motion of the ultrasonic tip 20 distal to the resonator 105. For example, as the transducer 44 expands and contracts, a vibration is created that is transmitted to the ultrasonic tip 20 via the horn 40. The portion of the ultrasonic tip 20 that is proximal to the resonator 105 experiences a longitudinal motion. The resonator 105 may then translates the longitudinal motion of the transducer 44 and horn 40 into a longitudinal and torsional torsion motion in the portion of the ultrasonic tip 20 that is distal to the resonator 105. The resonator 105 may comprise a non-homogeneous cross sectional region created by grooves in the outer surface of the ultrasonic tip 20. The grooves may be oriented in a generally spiral-like and helical configuration on the outer surface of the ultrasonic tip 20. This may be accomplished but cutting the grooves in a spiral-like or helical pattern on the outer surface of the ultrasonic tip 20. Alternatively, the spiral-like or helical pattern of the grooves may be accomplished by cutting straight grooves in the outer surface of the ultrasonic tip 20, wherein the grooves are generally parallel to the longitudinal axis of the ultrasonic tip 20, and the ultrasonic tip 20 may then be twisted to create the spiral-like or helical pattern of the grooves.

Referring to FIGS. 12-16, an example configuration of the tubing connector 22 for use with the ultrasonic handpiece 12 as part of the ultrasonic surgical handpiece assembly 10 is illustrated. The tubing connector 22 may comprise a base 24 including a distal end and a proximal end. The base 24 may be constructed of a rigid material such as a plastic. Alternatively, the base 24 may be constructed of a flexible material or resilient material such as an elastomer.

The base 24 may be configured to define one or two lumens 112, 114 that extend through the base 24. The lumens 112, 114 may define a fluid passageway through the base 24 of the tubing connector 22 and be configured to be in fluid communication with one or more conduits or lumens through the ultrasonic handpiece 12. For example, a first lumen 112 may be configured to be in fluid communication with the passageway that is formed by the conduit 42 of the horn 40 and the lumen 45 of the transducer 44 when the tubing connector 22 is coupled to the ultrasonic handpiece 12. Additionally, a second lumen 114 may be configured to be in fluid communication with the lumen 59 that is disposed within the ultrasonic handpiece 12 when the tubing connector 22 is coupled to the ultrasonic handpiece 12.

The base 24 may also define a groove 110 in a perimeter of the base 24 that extends between the distal end and the proximal end of the base 24. The groove 110 may be configured to receive the cable 30, wiring harness, or similar conductor that extends proximally from the proximal end of the ultrasonic handpiece 12. For example, the groove 110 of the tubing connector may be configured to receive and partially surround the cable 30, as illustrated in FIG. 1. The groove 110 may be shaped and/or configured to removably couple the base 24 of the tubing connector 22 to the cable 30 via a friction fit or interference fit. For example, the groove 110 may comprise a U-like or crescent shape, wherein the width of the opening of the groove 110 at the surface of the base 24 is less than the maximum width of the cable 30.

The tubing connector 22 may further comprise a resilient member 26 that extends proximally from the base 24 and is configured to receive the aspiration line 27. The resilient member 26 and base 24 may be formed as a unitary component, wherein the resilient member 26 defines a portion of the lumen 112 through the base 24. The resilient member 26 may be configured such that the aspiration line 27 may be inserted within the lumen 112 at the proximal end of the resilient member 26. The aspiration line 27 may for a friction fit within the lumen of the resilient member. Alternatively, the aspiration line 27 may be coupled to the resilient member 26 using a glue, epoxy, or similar adhesive configured to create a chemical bond.

While not illustrated, it is also contemplated that the resilient member 26 may be removably coupled to the base 24. For example, a distal end of the resilient member 26 may be configured to create a friction with the base 24 when inserted in the lumen 112.

While the figures illustrate the aspiration line 27 and/or the irrigation line 29 as being inserted directly within the lumens 112, 114 defined in the base 24 of the tubing connector 22, if is further contemplated that the aspiration line 27 and/or the irrigation line 29 may be coupled to the base 24 by a hose barb or similar fitting. For example, proximal end of a hose barb may inserted in the opening of the aspiration line 27 and/or the irrigation line 29. The proximal end of the hose barb may then be inserted within the respective lumens 112, 114 that are defined in the base 24. The hose barb(s) may be coupled to the base 24 via friction fit within the lumens 112, 114, or the hose barb(s) may be coupled to the base 24 using an epoxy, glue, sealant, or similar adhesive.

The base 24 may be configured to be removably coupled the proximal end of the ultrasonic handpiece 12 via and interference fit. The interference fit may be created between the coupling feature 56 of the irrigation tube 58 and the coupling portion 54 of the channel 53 and the respective lumens 112, 114. For example, the coupling feature 56 and coupling portion 54 may each comprise a hose barb or similar fitting configured to be inserted in the corresponding lumens 112, 114 to create a friction fit that removably secures the tubing connector 22 to the proximal end of the ultrasonic handpiece 12.

Alternatively, while not illustrated in the figures, it is contemplated that the distal end of the base 24 may comprise a retention feature such as a tab or finger configured to create a snap-fit with the proximal end of the ultrasonic handpiece 12. For example, the retention feature may comprise a tab or protrusion that encircles a perimeter of the distal end of the base 24 and is configured to engage the proximal end of the ultrasonic handpiece 12 to removably couple the tubing connector 22 to the ultrasonic handpiece 12 via a snap fit.

The tubing connector 22 may serve as a means of quickly attaching and detaching both the irrigation line 29 and the aspiration line 27 to the proximal end of the ultrasonic handpiece 12. Furthermore, the tubing connector 22 may removably secure the irrigation line and/or aspiration lines 29, 27 to the ultrasonic handpiece 12 in a manner that reduces the stress on the lines proximate the ultrasonic handpiece 12. The tubing connector 22 may reduce bending and/or kinking of the lines proximate the ultrasonic handpiece 12. For example, the resilient member may comprise a resilient material configured to support the aspiration line 17 and/or resist bending or kinking the aspiration line 17. Furthermore, the proximal offset created by the resilient member extending proximally from the base 24 offsets the location where the aspiration line 27 and the irrigation line 29 are coupled to the base 24. This may prevent tangling of the lines as the drape off the proximal end of the tubing connector 22. This serves to provide support to the lines 27, 29 to resists bending of the line 27, 29 proximate the ultrasonic handpiece 12 to reduce the occurrence of sharp bends in the lines 27, 29 that may restrict flow through the lines 27, 29.

Clauses:

i. A method of assembling an ultrasonic surgical handpiece without using separate irrigation connections to a tip sleeve, said method comprising:
   providing a housing including an irrigation conduit configured to communicate irrigation fluid through the ultrasonic surgical handpiece and an attachment region in the form of a recess in a distal end of the housing,
   providing an irrigation sleeve comprising a hub including a proximal portion and a distal portion, the proximal portion defining a protrusion extending proximally from the distal portion and sized to be inserted within the recess of the housing; and
   coupling the housing to the irrigation sleeve by inserting the protrusion into the recess to provide irrigation fluid to the irrigation sleeve without separately connecting an irrigation line to the irrigation sleeve.

ii. A sleeve for use with an ultrasonic handpiece including a coupling housing comprising a handpiece transceiver and configured to surround a portion of an ultrasonic tip including a cutting feature, said sleeve comprising:
   a hub comprising a proximal portion, a distal portion, and a first lumen extending through said hub;
   a tube body comprising a distal end and a proximal end, said tube body extending from said distal portion of said hub and configured to define a second lumen in fluid communication with said first lumen of said hub, said second lumen configured to surround the portion of the ultrasonic tip;
   a tube aperture in an interior surface of said second lumen, said tube aperture positioned at an intermediate point along said second lumen between said proximal end and distal end of said tube body and such that said tube aperture is facing inward towards said second lumen;

an irrigation conduit adjacent to said second lumen, said irrigation conduit configured to extend from said proximal end of said tube body to said tube aperture;

an irrigation aperture and a tip aperture in said first face, said tip aperture configured to be in communication with said first lumen;

an irrigation fitting positioned within said irrigation aperture of said first face of said hub and in fluid communication with said irrigation tube;

a cavity defined in said proximal portion of said hub, said cavity comprising an opening in a first surface; and a sleeve transceiver positioned within said cavity and configured to communicate with the corresponding handpiece transceiver.

iii. An ultrasonic handpiece assembly for use with an elongated cutting instrument/element, said assembly comprising:

an ultrasonic handpiece comprising:

a housing comprising a proximal end and an opposing distal end, said housing defining a volume, said distal end having a distal face;

a transducer configured to define a first conduit, said transducer at least partially disposed within said volume defined by said housing;

a horn comprising a first end and an opposing second end, said horn configured to be at least partially disposed within said volume defined by said housing;

a second conduit in said horn configured to extend between said first end and said second end of said horn;

an irrigation outlet fitting extending from said distal end of said housing and configured to discharge irrigation fluid from said housing;

a coupler on said second end of said horn configured to engage the elongated cutting instrument;

a recess in said distal end of said housing; and a handpiece transceiver comprising a handpiece coil;

an irrigation sleeve comprising:

a hub comprising a proximal portion and a distal portion, said proximal portion configured to define a protrusion sized to be inserted within said recess of said housing;

an abutment portion configured to contact said distal face of said ultrasonic handpiece when said protrusion is inserted in said recess of said housing;

a sleeve transceiver comprising a sleeve coil and a memory unit, the memory unit storing information pertaining to the optimal driving parameter for the elongated cutting instrument; and wherein said sleeve transceiver is located in a cavity defined in said hub such that second axis of said sleeve coil is aligned with the handpiece coil.

iv. A method of making a surgical handpiece with a flex circuit having an antenna, said method comprising:

providing an internal flex circuit having an antenna at a distal end of said internal flex circuit;

providing a first housing component and a second housing component, wherein the first and second housing components are injection molded such that one of the first and second housing components defines a void and one of the first and second housing components comprises an irrigation conduit configured to communicate irrigation fluid through the surgical handpiece;

positioning the internal flex circuit within the void of one of the first housing component and the second housing component;

securing the first housing component to the second housing component to fix the internal flex circuit into position; and overmolding the first housing component, the second housing component, and a portion of the internal flex circuit with an autocleaveable plastic to fix the location of the antenna of the internal flex circuit in the first and second housing components v. The method of clause iv, further comprising the initial step of injection molding the first housing component and the second housing component.

vi. The method of clause v, wherein the first housing component and the second housing component are injection molded to comprise corresponding channels extending longitudinally along the length of each of the first housing component and the second housing component, wherein the corresponding channels define the void when the first housing component and the second housing component are secured together.

vii. The method of clause vi, wherein the step of positioning the internal flex circuit within the void comprises inserting a portion of said internal flex circuit in the channel of the first housing component or the second housing component prior to securing the first housing component to the second housing component.

viii. The method of any of clauses iv-vii, further comprising the step of coupling a proximal end of the flex circuit to a processor, wherein said processor is configured to communicate with the antenna at the distal end of the flex circuit.

ix. A method of making a surgical handpiece with a flex circuit having an antenna, said method comprising:

providing an internal flex circuit having a sensor;

providing a first housing component and a second housing component, wherein the first and second housing components are injection molded such that one of the first and second housing components defines a void and one of the first and second housing components comprises an irrigation conduit configured to communicate irrigation fluid through the surgical handpiece;

positioning the internal flex circuit within the void of one of the first housing component and the second housing component;

securing the first housing component to the second housing component to fix the internal flex circuit into position; and overmolding the first housing component, the second housing component, and a portion of the internal flex circuit with an autocleaveable plastic to fix the location of the sensor of the internal flex circuit in the first and second housing components.

x. A sleeve for use with an ultrasonic handpiece including a coupling housing comprising a handpiece transceiver and configured to surround a portion of an ultrasonic tip including a cutting feature, said sleeve comprising:

a hub comprising a proximal portion, a distal portion, and a first lumen extending through said hub, said proximal portion having a first face configured to abut the ultrasonic handpiece and a second face positioned distally of said first face;

a tube body comprising a distal end and a proximal end, said tube body extending from said distal portion of said hub and configured to define a second lumen in fluid communication with said first lumen of said hub, said second lumen configured to surround the portion of the ultrasonic tip;

a tube aperture in an interior surface of said second lumen, said tube aperture positioned at an intermediate point along said second lumen between said proximal end and distal end of said tube body and such that said tube aperture is facing inward towards said second lumen;

an irrigation conduit adjacent to said second lumen, said irrigation conduit configured to extend from said proximal end of said tube body to said tube aperture;

an irrigation aperture and a tip aperture in said first face, said tip aperture configured to be in communication with said first lumen;

an irrigation fitting positioned within said irrigation aperture of said first face of said hub and in fluid communication with said irrigation conduit;

at least one retention finger protruding proximally from said first face, said retention finger configured to engage the coupling housing of the ultrasonic handpiece;

a cavity defined in said proximal portion of said hub, said cavity comprising an opening in a first surface; and a sleeve transceiver positioned within said cavity and configured to communicate with the corresponding handpiece transceiver.

xi. The sleeve of clause x, wherein said proximal portion comprises an asymmetrical shape and is configured to be inserted into the coupling housing of the ultrasonic handpiece.

xii. The sleeve of clause xi, wherein the proximal portion comprises:
  a first wall and a third wall oriented in parallel to one another;
  a second wall extending between said first wall and said third wall, said second wall oriented to be generally perpendicular to said first wall and said third wall;
  a fourth wall extending between said first wall and said third wall opposite said second wall, said fourth wall comprising a generally arced shape;
  wherein said first wall, said second wall, said third wall, and said fourth wall define said asymmetrical shape of said proximal portion.

xiii. The sleeve of any of clauses x-xii, wherein said first face and said second face are oriented in the same direction.

xiv. The sleeve of any of clauses x-xiii, wherein said first face and said second face are oriented to be parallel to one another.

xv. The sleeve of any of clauses x-xiv, wherein said irrigation fitting defines a third lumen configured to receive a corresponding barb of the ultrasonic handpiece to provide irrigation fluid to said sleeve.

xvi. The sleeve of any of clauses x-xv, further comprising a seal positioned within said opening of said cavity, said seal configured to secure said sleeve transceiver within said cavity.

xvii. The sleeve of any of clauses x-xvi, wherein said sleeve transceiver comprises a first axis and said sleeve transceiver is positioned within said cavity such that said first axis is generally perpendicular to a second axis defined by said first face.

xviii. The sleeve of any of clauses x-xvii, wherein said sleeve transceiver further comprises a memory, said memory configured to store data related to one or more characteristics related to the ultrasonic tip.

xix. An ultrasonic surgical handpiece for use with an ultrasonic tip assembly including a sleeve comprising at least one retention member, said ultrasonic surgical handpiece comprising:

a housing comprising a proximal end and an opposing distal end, said housing configured to define a volume;

a transducer at least partially disposed within said volume defined by said housing;

a horn comprising a first end and an opposing second end and configured to be at least partially disposed within said volume defined by said housing, said first end of said horn operatively coupled to said transducer;

wherein said transducer is configured to vibrate/oscillate said horn when operated;

an attachment region formed in said distal end of said housing, said attachment region defining a recess comprising a face and a plurality of side walls configured to receive the sleeve;

an attachment element in said face of said recess, said attachment element configured to receive the at least one retention member of the sleeve to removably couple the sleeve to said ultrasonic surgical handpiece;

a first fitting extending from said face of said recess and configured to removably couple with the sleeve to provide irrigation to the sleeve; and wherein said second end of said horn is configured to protrude from said face.

xx. The ultrasonic surgical handpiece of clause xix, wherein said plurality of side walls comprises a first wall, a second wall, a third wall, and a fourth wall extending from an outer perimeter of said face;
  wherein said first wall and said third wall are positioned to be generally parallel to one another; and
  wherein said second wall and said fourth wall are positioned to be generally parallel to one another and configured to extend between opposing ends of said first wall and said third wall.

xxi. The ultrasonic surgical handpiece of clause xx, wherein said fourth wall comprises a generally hemispherical shape and extends between said first wall and said third wall opposite said second wall.

xxii. The ultrasonic surgical handpiece of clauses xx or xxi, wherein said second wall further comprises a cavity configured to embed a handpiece transceiver within said second wall, said handpiece transceiver comprising an axis;
  wherein said handpiece transceiver is positioned within said cavity such that said axis is parallel to an interior surface of said second wall.

xxiii. The ultrasonic surgical handpiece of any of clauses xix-xxii, wherein said first fitting is a male fitting configured to be received by a corresponding female fitting of the sleeve.

xxiv. The ultrasonic surgical handpiece of any of clauses xix-xxiii, wherein said attachment element comprises an aperture in said face, said aperture configured to provide a friction fit with a tab on the at least one retention member of the sleeve.

xxv. An ultrasonic handpiece assembly for use with an elongated cutting instrument including an aspiration lumen extending the length of the elongated cutting instrument, said assembly comprising:
  an ultrasonic handpiece comprising:
    a housing comprising a proximal end and an opposing distal end, said housing defining a volume, said distal end having a distal face;
    a transducer configured to define a first conduit, said transducer at least partially disposed within said volume defined by said housing;

a horn comprising a first end and an opposing second end, said horn configured to be at least partially disposed within said volume defined by said housing;

a second conduit in said horn configured to extend between said first end and said second end of said horn;

a threaded coupler on said second end of said horn configured to extend from said distal end of said housing and removably couple said horn to the elongated cutting instrument;

an irrigation outlet fitting extending from said distal end of said housing and configured to discharge irrigation fluid from said housing;

an irrigation sleeve comprising:
a hub defining a first lumen and comprising an irrigation inlet fitting, said irrigation inlet fitting configured to engage said irrigation outlet fitting to receive irrigation fluid discharged from said ultrasonic handpiece;

a sleeve body extending distally from said hub, said sleeve body defining a second lumen configured to surround a portion of the elongated cutting instrument when the elongated cutting instrument is inserted into said irrigation sleeve;

a tube aperture in an interior surface of said second lumen, said tube aperture positioned at an intermediate point along said second lumen between a proximal end and a distal end of said sleeve body such that said tube aperture is facing toward said second lumen to provide irrigation fluid to a surgical site and to cool the elongated cutting instrument;

an irrigation conduit running adjacent to said second lumen, said irrigation conduit configured to extend from said irrigation inlet fitting of said sleeve body to said tube aperture to create a fluid passageway for communicating irrigation fluid to the elongated cutting instrument;

wherein said irrigation outlet fitting on said housing is configured to engage the irrigation inlet fitting on said irrigation sleeve when said irrigation sleeve is coupled to said housing such that the irrigation fluid flows entirely within the ultrasonic handpiece and said hub; and wherein said first end of said horn is operatively coupled to said transducer such that said first conduit of said transducer and said second conduit of said horn define a continuous passageway extending from said proximal end to said distal end of said housing.

xxvi. The ultrasonic handpiece assembly of clause xxv, wherein said ultrasonic handpiece further comprises an irrigation inlet fitting located on the proximal end of the housing and is configured to receive irrigation fluid from an irrigation source.

xxvii. The ultrasonic handpiece assembly of clause xxv or xxvi, wherein said threaded coupler is configured to removably couple said horn to the elongated cutting instrument such that said continuous passageway extending from said proximal end to said distal end of said housing is in fluid communication with the aspiration lumen of the elongated cutting instrument to allow for removal of ablated tissue through the aspiration lumen when a vacuum is applied to said continuous passageway.

xxviii. The ultrasonic handpiece assembly of any of clauses xxv-xxvii, wherein said hub further comprises:

a proximal portion and a distal portion, said proximal portion having a first face configured to abut the ultrasonic handpiece and a second face positioned distally of said first face;

at least one retention finger protruding proximally from said first face, said retention finger configured to engage the housing of the ultrasonic handpiece;

a cavity defined in said proximal portion of said hub, said cavity comprising an opening in a first surface; and a sleeve transceiver positioned within said cavity and configured to communicate with a corresponding handpiece transceiver.

xxix. The ultrasonic handpiece assembly of clause xxviii, wherein said housing further comprises:

an attachment region formed in said distal end of said housing, said attachment region defining a recess comprising a third face and a plurality of side walls configured to receive said hub of said irrigation sleeve;

an attachment element in said third face of said recess, said attachment element configured to receive said retention finger of said irrigation sleeve to removably couple said irrigation sleeve to said ultrasonic handpiece;

wherein said irrigation outlet fitting is configured to extend from said third face of said recess to removably couple with said irrigation sleeve to provide irrigation fluid to said irrigation sleeve; and wherein said second end of said horn is configured to protrude from said face.

xxx. The ultrasonic handpiece assembly of any of clauses xxv-xxix, wherein said irrigation sleeve further comprises a seal positioned within said second lumen and configured to abut said interior surface of said second lumen to space the elongated cutting instrument from said interior surface of said second lumen.

xxxi. An ultrasonic handpiece assembly for use with an elongated cutting instrument, said assembly comprising:

an ultrasonic handpiece comprising:
a housing comprising a proximal end and an opposing distal end, said housing defining a volume, said distal end having a distal face;

a transducer configured to define a first conduit, said transducer at least partially disposed within said volume defined by said housing;

a horn comprising a first end and an opposing second end, said horn configured to be at least partially disposed within said volume defined by said housing;

a second conduit in said horn configured to extend between said first end and said second end of said horn;

an irrigation outlet fitting extending from said distal end of said housing and configured to discharge irrigation fluid from said housing;

a threaded coupler on said second end of said horn configured to engage the elongated cutting instrument;

a recess in said distal end of said housing, said recess comprising a recessed face and a plurality of side walls configured to define an asymmetrical shape; and a handpiece transceiver comprising a handpiece coil comprising a first axis, said handpiece transceiver positioned within one of said plurality of side walls;

an irrigation sleeve comprising:
a hub comprising a proximal portion and a distal portion, said proximal portion configured to define an asymmetrical protrusion extending proximally from said distal portion and sized to be inserted within said recess of said housing;

an abutment portion configured to contact said distal face of said ultrasonic handpiece when said asymmetrical protrusion is inserted in said recess of said housing, said asymmetrical protrusion configured to ensure proper alignment of said irrigation sleeve with said housing;

a sleeve transceiver comprising a sleeve coil and a memory unit, the memory unit for storing information pertaining to the optimal driving parameter for the elongated cutting instrument, said sleeve coil having a second axis; and wherein said sleeve transceiver is located in a cavity defined in said asymmetrical protrusion of said hub such that second axis of said sleeve coil is oriented in parallel to said first axis of said handpiece coil.

xxxii. The ultrasonic handpiece assembly of clause xxxi, wherein said irrigation sleeve further comprises a sleeve body extending distally from said distal portion of said hub, said sleeve body defining a second lumen configured to surround a portion of the elongated cutting instrument when the elongated cutting instrument is inserted into said irrigation sleeve; and a tube aperture in an interior surface of said second lumen, said tube aperture positioned at an intermediate point along said second lumen between a proximal end and a distal end of said sleeve body such that said tube aperture is facing toward said second lumen to provide irrigation fluid to a surgical site and to cool the elongated cutting instrument.

xxxiii. The ultrasonic handpiece assembly of clause xxxii, wherein said irrigation sleeve further comprises a seal positioned within said second lumen and configured to abut said interior surface of said second lumen to space the elongated cutting instrument from said irrigation sleeve.

xxxiv. The ultrasonic handpiece assembly of clause xxxiii, wherein said asymmetrical protrusion further comprises at least one retention finger protruding proximally from said asymmetrical protrusion;

wherein said at least one retention finger and said seal cooperate to ensure said irrigation sleeve is appropriately spaced from the elongated cutting instrument when said ultrasonic handpiece is coupled to said irrigation sleeve.

xxxv. The ultrasonic handpiece assembly of any of clauses xxxi-xxxiv, further comprising an elongated cutting instrument having a second threaded coupler at a proximal end and a distal end comprising a cutting surface, said second threaded coupler of the elongated cutting instrument configured to removably couple to said threaded coupler of said horn.

xxxvi. A method of assembling an ultrasonic surgical handpiece without using separate irrigation connections to a tip sleeve, said method comprising:

providing a housing including an irrigation conduit configured to communicate irrigation fluid through the ultrasonic surgical handpiece and an attachment region in a distal end of the housing, the attachment region comprising:

a recessed face and a plurality of side walls configured to define an asymmetrical void; and an attachment element in the attachment region;

providing an irrigation sleeve comprising a hub including a proximal portion and a distal portion, the proximal portion comprising one or more retention fingers and configured to define an asymmetrical protrusion extending proximally from the distal portion and sized to be inserted within the recess of the housing; and coupling the housing to the irrigation sleeve by inserting the asymmetrical protrusion into the asymmetrical void to engage the one or more retention fingers with the attachment element to provide irrigation fluid to the irrigation sleeve without separately connecting an irrigation line to the irrigation sleeve.

xxxvii. The method of clause xxxvi, further comprising the step of providing a cutting tip, the cutting tip comprising a threaded coupler at a distal end configured to removably secure the cutting tip to the housing and a cutting element at a proximal end; and coupling the cutting tip to the housing prior to the step of coupling the housing to the irrigation sleeve.

xxxviii. The method of clause xxxvi or xxxvii, wherein the step of coupling the housing to the irrigation sleeve further comprises inserting a first irrigation fitting on a distal end of the irrigation conduit of the housing into a corresponding second irrigation fitting on the irrigation sleeve as the asymmetrical protrusion is inserted into the asymmetrical void, wherein the second irrigation fitting is in fluid communication with a second conduit of the sleeve configured to provide irrigation fluid to a cutting tip.

xxxix. A tubing connector for integrally connecting an irrigation line, an aspiration line, and a conductor to a proximal portion of an ultrasonic surgical handpiece wherein the ultrasonic surgical handpiece comprises an irrigation fitting and an aspiration fitting that extend proximally from the proximal portion of the handpiece, said tubing connector comprising:

a base comprising a distal end and a proximal end;

a first lumen in said base configured to create a fluid passageway through said base that extends from said distal end to said proximal end of said base, a said first lumen is configured to receive the aspiration line proximate said proximal end of said base;

wherein said base defines a groove in a perimeter of said base that extends between said proximal end to said distal end of said base, said groove configured to receive the conductor;

wherein a portion of said first lumen proximate said distal end of said base is configured to removably couple with the aspiration fitting the ultrasonic surgical handpiece via a friction fit; and wherein said tubing connector is configured to reduce strain of the irrigation line and the aspiration line when coupled to the surgical handpiece.

xl. The tubing connector of clause xxxix, wherein said base further comprises:

a second lumen in said base, said second lumen configured to create a second fluid passageway through said base that extends from said distal end to said proximal end of said base, a said second lumen is configured to receive the irrigation line proximate said proximal end of said base;

wherein a portion of said second lumen proximate said distal end of said base is configured to removably couple with the irrigation fitting the ultrasonic surgical handpiece via a friction fit.

xli. The tubing connector of clause 31, wherein said base further comprises a resilient member extending proximally from said proximal end of said base, said resilient member configured to define a portion of said first lumen;

wherein said resilient member is configured to extend proximally from said base to proximally offset the position the aspiration line couples to said first lumen relative to the position the irrigation line couples to said second lumen.

xlii. The tubing connector of clause xxxix or xl, wherein said base further comprises a resilient member extending proximally from said proximal end of said base, said resilient member configured to define a portion of said first lumen.

xliii. The tubing connector of clause xxxix or xl, wherein said base further comprises a resilient member extending proximally from said proximal end of said base, said resilient member configured to define a portion of said first lumen; and
wherein said resilient member is constructed from a resilient material configured to support the aspiration line when coupled to said tubing connector.

xliv. A tubing connector for integrally connecting an irrigation line, an aspiration line, and a conductor to a proximal portion of an ultrasonic surgical handpiece, said tubing connector comprising:
a base comprising a proximal region and a distal region, said base constructed of a resilient material;
a first lumen through said base that extends from said proximal end to said distal end configured to create a first fluid pathway to the proximal portion of the surgical handpiece, said first lumen comprising a first coupler proximate said proximal end of said base configured to receive the irrigation line;
a second lumen through said base that extends from said proximal end to said distal end configured to create a second fluid pathway to the proximal portion of the surgical handpiece, said second lumen comprising a second coupler proximate said proximal end of said base configured to receive the aspiration line;
wherein said base defines a groove in an outer perimeter of said base that extends between said proximal region to said distal region of said base, said groove configured to receive the conductor; and
wherein said tubing connector is configured to reduce strain of the aspiration line and the irrigation line when connected to the surgical handpiece.

xlv. The tubing connector of clause xliv, wherein said base further comprises a resilient member extending proximally from said proximal region of said base, said resilient member configured to define a portion of said first lumen.

xlvi. An ultrasonic surgical handpiece comprising:
a housing defining a cavity, said housing defining a proximal aperture and a distal aperture;
a transducer comprising a distal end and a proximal end disposed within said cavity of said housing, said transducer configured to expand and contract along a longitudinal axis of the transducer;
a tube defining a transducer lumen comprising a distal portion and a proximal portion, said lumen being configured to extend from said proximal end to said distal end of said transducer and be oriented to be generally parallel to said longitudinal axis;
a barrier member having a shell portion wholly within said cavity and a channel portion that extends proximally from said shell portion and extends through said proximal aperture, the shell portion defining a shell lumen configured to encase said transducer positioned within said housing, the channel portion configured to rout aspirated fluid from said transducer lumen to a suction line;
a horn at least partially disposed within said housing, said horn coupled to said distal end of said transducer, said horn defining a horn lumen that is in fluid communication with said transducer lumen when said horn is coupled to said transducer;
a rear seal positioned between said proximal end of said transducer and an interior surface of said cavity, said rear seal configured to abut said proximal end of said transducer and define a first aperture that engages an exterior surface of said tube and an interior surface of said barrier member, said rear seal is positioned between said shell portion and said channel portion of said barrier member such that fluid cannot enter said shell portion of said barrier member;
a front seal positioned disposed radially about an exterior surface of said horn, said front seal;
a potting seal positioned between said transducer and a distal end of said shell portion of said barrier member, said potting seal configured to abut said distal end of said transducer and define a second aperture for receiving said coupling feature of said horn;
wherein said rear seal is configured to prevent moisture ingress into said cavity proximate the proximal end of said transducer; and
wherein said potting seal is configured to prevent moisture ingress into said cavity proximate said distal end of said transducer.

xlvii. The ultrasonic surgical handpiece of clause xlvi, wherein said front seal comprises a plurality of bumps configured to prevent ingress of moisture into said cavity between said horn and said housing.

xlviii. The ultrasonic surgical handpiece of clause xlvi or xlvii, wherein said potting seal is configured to prevent potting from entering said cavity.

xlix. The ultrasonic surgical handpiece of any of clauses xlvi-xlviii, wherein said rear seal and said potting seal comprise a resilient material configured to support said transducer within said cavity as said transducer expands and contracts.

Several embodiments have been discussed in the foregoing description. However, the embodiments discussed herein are not intended to be exhaustive or limit the invention to any particular form. For example, while the example configurations describe the surgical instrument as an ultrasonic handpiece, it is further contemplated that the features and concepts described with regard to the ultrasonic handpiece may be applied to other medical or surgical instruments. This similarly applies to the ultrasonic tip 20, which may further include blades, drill bits, rotating burs, open-window shavers, and the like. The terminology which has been used is intended to be in the nature of words of description rather than of limitation. Many modifications and variations are possible in light of the above teachings and the invention may be practiced otherwise than as specifically described.

What is claimed is:

1. A sleeve for use with an ultrasonic handpiece including a coupling housing comprising a handpiece transceiver and configured to surround a portion of an ultrasonic tip including a cutting feature, said sleeve comprising:
a hub comprising a proximal portion, a distal portion, and a first lumen extending through said hub, said proximal portion having a first face configured to abut the ultrasonic handpiece and a second face positioned distally of said first face;

a tube body comprising a distal end and a proximal end, said tube body extending from said distal portion of said hub and configured to define a second lumen in fluid communication with said first lumen of said hub, said second lumen configured to surround the portion of the ultrasonic tip;

a tube aperture in an interior surface of said second lumen, said tube aperture positioned at an intermediate point along said second lumen between said proximal end and distal end of said tube body and such that said tube aperture is facing inward towards said second lumen;

an irrigation conduit adjacent to said second lumen, said irrigation conduit configured to extend from said proximal end of said tube body to said tube aperture;

an irrigation aperture and a tip aperture in said first face, said tip aperture configured to be in communication with said first lumen;

an irrigation fitting positioned within said irrigation aperture of said first face of said hub and in fluid communication with said irrigation conduit;

at least one retention finger protruding proximally from said first face, said retention finger configured to engage the coupling housing of the ultrasonic handpiece;

a cavity defined in said proximal portion of said hub, said cavity comprising an opening in a surface of the hub; and a sleeve transceiver positioned within said cavity and configured to communicate with the corresponding handpiece transceiver.

2. The sleeve of claim 1, wherein said proximal portion comprises an asymmetrical shape and is configured to be inserted into the coupling housing of the ultrasonic handpiece.

3. The sleeve of claim 2, wherein the proximal portion comprises:
a first wall and a third wall oriented in parallel to one another;
a second wall extending between said first wall and said third wall, said second wall oriented to be generally perpendicular to said first wall and said third wall; and
a fourth wall extending between said first wall and said third wall opposite said second wall, said fourth wall comprising a generally arced shape,
wherein said first wall, said second wall, said third wall, and said fourth wall define said asymmetrical shape of said proximal portion.

4. The sleeve of claim 1, wherein said first face and said second face are oriented in the same direction.

5. The sleeve of claim 1, wherein said first face and said second face are oriented to be parallel to one another.

6. The sleeve of claim 1, wherein said irrigation fitting defines a third lumen configured to receive a corresponding barb of the ultrasonic handpiece to provide irrigation fluid to said sleeve.

7. The sleeve of claim 1, further comprising a seal positioned within said opening of said cavity, said seal configured to secure said sleeve transceiver within said cavity.

8. The sleeve of claim 1, wherein said sleeve transceiver comprises a first axis and said sleeve transceiver is positioned within said cavity such that said first axis is generally perpendicular to a second axis defined by said first face.

9. The sleeve of claim 1, wherein said sleeve transceiver further comprises a memory, said memory configured to store data related to one or more characteristics related to the ultrasonic tip.

10. An ultrasonic handpiece assembly for use with an elongated cutting instrument including an aspiration lumen extending the length of the elongated cutting instrument, said assembly comprising:
an ultrasonic handpiece comprising:
a housing comprising a proximal end and an opposing distal end, said housing defining a volume;
a transducer configured to define a first conduit, said transducer at least partially disposed within said volume defined by said housing;
a horn comprising a first end and an opposing second end, said horn configured to be at least partially disposed within said volume defined by said housing;
a second conduit in said horn configured to extend between said first end and said second end of said horn;
a threaded coupler on said second end of said horn configured to extend from said distal end of said housing and removably couple said horn to the elongated cutting instrument; and
an irrigation outlet fitting extending from said distal end of said housing and configured to discharge irrigation fluid from said housing; and
an irrigation sleeve comprising:
a hub defining a first lumen and comprising an irrigation inlet fitting, said irrigation inlet fitting configured to engage said irrigation outlet fitting to receive irrigation fluid discharged from said ultrasonic handpiece;
a sleeve body extending distally from said hub, said sleeve body defining a second lumen configured to surround a portion of the elongated cutting instrument when the elongated cutting instrument is inserted into said irrigation sleeve;
a tube aperture in an interior surface of said second lumen, said tube aperture positioned at an intermediate point along said second lumen between a proximal end and a distal end of said sleeve body such that said tube aperture is facing toward said second lumen to provide irrigation fluid to a surgical site and to cool the elongated cutting instrument; and
an irrigation conduit running adjacent to said second lumen, said irrigation conduit configured to extend from said irrigation inlet fitting of said hub to said tube aperture to create a fluid passageway for communicating irrigation fluid to the elongated cutting instrument,
wherein said irrigation outlet fitting on said housing is configured to engage the irrigation inlet fitting on said irrigation sleeve when said irrigation sleeve is coupled to said housing such that the irrigation fluid flows entirely within the ultrasonic handpiece and said hub, and
wherein said first end of said horn is operatively coupled to said transducer such that said first conduit of said transducer and said second conduit of said horn define a continuous passageway extending from said proximal end to said distal end of said housing.

11. The ultrasonic handpiece assembly of claim 10, wherein said ultrasonic handpiece further comprises an irrigation inlet fitting located on the proximal end of the housing and is configured to receive irrigation fluid from an irrigation source.

12. The ultrasonic handpiece assembly of claim 10, wherein said threaded coupler is configured to removably couple said horn to the elongated cutting instrument such that said continuous passageway extending from said proximal end to said distal end of said housing is in fluid communication with the aspiration lumen of the elongated cutting instrument to allow for removal of ablated tissue through the aspiration lumen when a vacuum is applied to said continuous passageway.

13. The ultrasonic handpiece assembly of claim 10, wherein said hub further comprises:
  a proximal portion and a distal portion, said proximal portion having a first face configured to abut the ultrasonic handpiece and a second face positioned distally of said first face;
  at least one retention finger protruding proximally from said first face, said retention finger configured to engage the housing of the ultrasonic handpiece;
  a cavity defined in said proximal portion of said hub, said cavity comprising an opening in a surface of the hub; and
  a sleeve transceiver positioned within said cavity and configured to communicate with a corresponding handpiece transceiver.

14. The ultrasonic handpiece assembly of claim 13, wherein said housing further comprises:
  an attachment region formed in said distal end of said housing, said attachment region defining a recess comprising a third face and a plurality of side walls configured to receive said hub of said irrigation sleeve; and
  an attachment element in said third face of said recess, said attachment element configured to receive said retention finger of said irrigation sleeve to removably couple said irrigation sleeve to said ultrasonic handpiece,
  wherein said irrigation outlet fitting is configured to extend from said third face of said recess to removably couple with said irrigation sleeve to provide irrigation fluid to said irrigation sleeve, and
  wherein said second end of said horn is configured to protrude from said third face.

15. The ultrasonic handpiece assembly of claim 10, wherein said irrigation sleeve further comprises a seal positioned within said second lumen and configured to abut said interior surface of said second lumen to space the elongated cutting instrument from said interior surface of said second lumen.

16. An ultrasonic handpiece assembly for use with an elongated cutting instrument, said assembly comprising:
  an ultrasonic handpiece comprising:
    a housing comprising a proximal end and an opposing distal end, said housing defining a volume, said distal end having a distal face;
    a transducer configured to define a first conduit, said transducer at least partially disposed within said volume defined by said housing;
    a horn comprising a first end and an opposing second end, said horn configured to be at least partially disposed within said volume defined by said housing;
    a second conduit in said horn configured to extend between said first end and said second end of said horn;
    an irrigation outlet fitting extending from said distal end of said housing and configured to discharge irrigation fluid from said housing;
    a threaded coupler on said second end of said horn configured to engage the elongated cutting instrument;
    a recess in said distal end of said housing, said recess comprising a recessed face and a plurality of side walls configured to define an asymmetrical shape; and
    a handpiece transceiver comprising a handpiece coil comprising a first axis, said handpiece transceiver positioned within one of said plurality of side walls; and
  an irrigation sleeve comprising:
    a hub comprising a proximal portion and a distal portion, said proximal portion configured to define an asymmetrical protrusion extending proximally from said distal portion and sized to be inserted within said recess of said housing;
    an abutment portion configured to contact said distal face of said ultrasonic handpiece when said asymmetrical protrusion is inserted in said recess of said housing, said asymmetrical protrusion configured to ensure proper alignment of said irrigation sleeve with said housing; and
    a sleeve transceiver comprising a sleeve coil and a memory unit, the memory unit storing information pertaining to an optimal driving parameter for the elongated cutting instrument, said sleeve coil having a second axis,
    wherein said sleeve transceiver is located in a cavity defined in said asymmetrical protrusion of said hub such that the second axis of said sleeve coil is oriented in parallel to said first axis of said handpiece coil when said asymmetrical protrusion is inserted in said recess of said housing.

17. The ultrasonic handpiece assembly of claim 16, wherein said irrigation sleeve further comprises:
  a sleeve body extending distally from said distal portion of said hub, said sleeve body defining a second lumen configured to surround a portion of the elongated cutting instrument when the elongated cutting instrument is inserted into said irrigation sleeve; and
  a tube aperture in an interior surface of said second lumen, said tube aperture positioned at an intermediate point along said second lumen between a proximal end and a distal end of said sleeve body such that said tube aperture is facing toward said second lumen to provide irrigation fluid to a surgical site and to cool the elongated cutting instrument.

18. The ultrasonic handpiece assembly of claim 17, wherein said irrigation sleeve further comprises a seal positioned within said second lumen and configured to abut said interior surface of said second lumen to space the elongated cutting instrument from said irrigation sleeve.

19. The ultrasonic handpiece assembly of claim 18, wherein said irrigation sleeve further comprises at least one retention finger protruding proximally from said asymmetrical protrusion, and
  wherein said at least one retention finger and said seal cooperate to ensure said irrigation sleeve is appropriately spaced from the elongated cutting instrument when said ultrasonic handpiece is coupled to said irrigation sleeve.

20. The ultrasonic handpiece assembly of claim 16, further comprising an elongated cutting instrument having a second threaded coupler at a proximal end and a distal end comprising a cutting surface, said second threaded coupler of the elongated cutting instrument configured to removably couple to said threaded coupler of said horn.

\* \* \* \* \*